(12) United States Patent
Srinivasan et al.

(10) Patent No.: US 9,539,361 B2
(45) Date of Patent: Jan. 10, 2017

(54) PROSTHETIC DEVICES

(75) Inventors: Satchit Srinivasan, Alpharetta, GA (US); Nikica Maljkovic, New Orleans, LA (US); Romana B. Chavers, Kiln, MS (US); Mohammad Jamal El-Hibri, Atlanta, GA (US); Roy L. Carter, San Ramon, CA (US); David B. Thomas, Suwanee, GA (US); Leslie J. Myrick, Suwanee, GA (US); Todd S. Rushing, Clinton, MS (US)

(73) Assignee: SOLVAY SPECIALTY POLYMERS USA, L.L.C., Alpharetta, GA (US)

( * ) Notice: Subject to any disclaimer, the term of this patent is extended or adjusted under 35 U.S.C. 154(b) by 1682 days.

(21) Appl. No.: 12/719,181

(22) Filed: Mar. 8, 2010

(65) Prior Publication Data
US 2010/0273957 A1 Oct. 28, 2010

Related U.S. Application Data

(63) Continuation-in-part of application No. PCT/EP2008/061947, filed on Sep. 9, 2008, which is a continuation-in-part of application No. PCT/EP2008/061948, filed on Sep. 9, 2008.

(60) Provisional application No. 60/971,314, filed on Sep. 11, 2007, provisional application No. 60/971,934, filed on Sep. 13, 2007.

(51) Int. Cl.
| | | |
|---|---|---|
| *C08L 61/00* | (2006.01) |
| *A61L 27/18* | (2006.01) |
| *A61L 27/26* | (2006.01) |
| *A61L 27/34* | (2006.01) |
| *A61F 2/28* | (2006.01) |
| *A61L 27/44* | (2006.01) |
| *C08L 81/00* | (2006.01) |
| *A61B 19/00* | (2006.01) |

(52) U.S. Cl.
CPC .................. *A61L 27/18* (2013.01); *A61F 2/28* (2013.01); *A61L 27/26* (2013.01); *A61L 27/34* (2013.01); *A61L 27/44* (2013.01); *A61L 27/446* (2013.01); *C08G 2261/312* (2013.01)

(58) Field of Classification Search
CPC ....................................................... C08L 61/00
USPC .................................. 525/471, 535; 128/898
See application file for complete search history.

(56) References Cited

U.S. PATENT DOCUMENTS

| 3,634,355 A | 1/1972 | Barr et al. |
| 4,008,203 A | 2/1977 | Jones et al. |
| 4,108,837 A | 8/1978 | Johnson et al. |

(Continued)

FOREIGN PATENT DOCUMENTS

| BE | 1015402 A6 | 3/2005 |
| CA | 847963 A | 7/1970 |

(Continued)

OTHER PUBLICATIONS

U.S. Appl. No. 12/061,442 claims.*

(Continued)

*Primary Examiner* — Duc Truong
(74) *Attorney, Agent, or Firm* — Oblon, McClelland, Maier & Neustadt, L.L.P.

(57) ABSTRACT

A prosthetic device comprising at least one part consisting of a polymer composition comprising at least one polyarylene (P1) and at least one polyarylether selected from the group consisting of poly(aryl ether ketone)s (P2) and poly(aryl ether sulfone)s (P3).

16 Claims, 2 Drawing Sheets

(56) References Cited

U.S. PATENT DOCUMENTS

| | | | |
|---|---|---|---|
| 4,164,794 A | 8/1979 | Spector et al. |
| 4,175,175 A | 11/1979 | Farnham et al. |
| 4,176,222 A | 11/1979 | Cinderey et al. |
| 4,351,069 A | 9/1982 | Ballintyn et al. |
| 4,662,887 A | 5/1987 | Turner et al. |
| 5,064,439 A | 11/1991 | Chang et al. |
| 5,176,710 A | 1/1993 | Hahn et al. |
| 5,181,930 A | 1/1993 | Dumbleton et al. |
| 5,219,363 A | 6/1993 | Crowninshield et al. |
| 5,227,457 A | 7/1993 | Marrocco et al. |
| 5,236,457 A | 8/1993 | Devanathan |
| 5,370,696 A | 12/1994 | Jamison et al. |
| 5,397,365 A | 3/1995 | Trentacosta |
| 5,443,512 A | 8/1995 | Parr et al. |
| 5,539,048 A | 7/1996 | Gagne et al. |
| 5,565,543 A | 10/1996 | Marrocco, III et al. |
| 5,646,231 A | 7/1997 | Marrocco, III et al. |
| 5,654,392 A | 8/1997 | Marrocco, III et al. |
| 5,659,005 A | 8/1997 | Marrocco, III et al. |
| 5,668,245 A | 9/1997 | Marrocco, III et al. |
| 5,670,564 A | 9/1997 | Gagne et al. |
| 5,721,335 A | 2/1998 | Marrocco, III et al. |
| 5,756,581 A | 5/1998 | Marrocco, III et al. |
| 5,760,131 A | 6/1998 | Marrocco, III et al. |
| 5,782,930 A | 7/1998 | Lin et al. |
| 5,824,744 A | 10/1998 | Gagne et al. |
| 5,827,927 A | 10/1998 | Gagne et al. |
| 5,869,592 A | 2/1999 | Gagne et al. |
| 5,872,159 A | 2/1999 | Cougoulic et al. |
| 5,886,130 A | 3/1999 | Trimmer et al. |
| 6,087,467 A | 7/2000 | Marrocco, III et al. |
| 6,566,484 B2 | 5/2003 | Gharda et al. |
| 6,585,755 B2 | 7/2003 | Jackson et al. |
| 6,602,293 B1 | 8/2003 | Biermann et al. |
| 7,419,714 B1 | 9/2008 | Magerl et al. |
| 2002/0099449 A1 | 7/2002 | Speitling |
| 2002/0107577 A1 | 8/2002 | Storer et al. |
| 2002/0111691 A1 | 8/2002 | Wang et al. |
| 2002/0115742 A1 | 8/2002 | Trieu et al. |
| 2002/0120336 A1 | 8/2002 | Santilli |
| 2002/0173850 A1 | 11/2002 | Brodke et al. |
| 2003/0004563 A1 | 1/2003 | Jackson et al. |
| 2003/0130476 A1 | 7/2003 | Kemmish et al. |
| 2003/0135275 A1 | 7/2003 | Garcia et al. |
| 2003/0195327 A1 | 10/2003 | King |
| 2004/0059356 A1 | 3/2004 | Gingras |
| 2004/0158324 A1 | 8/2004 | Lange |
| 2004/0249471 A1 | 12/2004 | Bindseil et al. |
| 2005/0136764 A1 | 6/2005 | Sherman et al. |
| 2005/0214492 A1 | 9/2005 | Zhong et al. |
| 2005/0228498 A1 | 10/2005 | Andres |
| 2006/0116774 A1 | 6/2006 | Jones et al. |
| 2006/0200245 A1 | 9/2006 | Trieu |
| 2006/0241759 A1 | 10/2006 | Trieu |
| 2006/0247638 A1 | 11/2006 | Trieu |
| 2007/0111165 A1 | 5/2007 | Wallick et al. |
| 2008/0293840 A1 | 11/2008 | Maljkovic et al. |
| 2008/0312387 A1 | 12/2008 | El-Hibri et al. |

FOREIGN PATENT DOCUMENTS

| | | |
|---|---|---|
| CN | 1582860 A | 2/2005 |
| CN | 1593356 A | 3/2005 |
| DE | 19728131 A1 | 1/1999 |
| DE | 19823737 A1 | 12/1999 |
| DE | 10256345 C1 | 12/2003 |
| EP | 0021682 A1 | 1/1981 |
| EP | 171884 A1 | 2/1986 |
| EP | 0598450 A1 | 5/1994 |
| EP | 0761242 A1 | 3/1997 |
| EP | 1813292 A1 | 8/2007 |
| GB | 2259253 A | 3/1993 |
| GB | 2319962 A | 6/1998 |
| WO | WO 93/04099 A1 | 3/1993 |
| WO | WO 93/14055 A1 | 7/1993 |
| WO | WO 96/39455 A1 | 12/1996 |
| WO | WO02070031 A1 | 9/2002 |
| WO | WO02071959 A1 | 9/2002 |
| WO | WO2004004592 A1 | 1/2004 |
| WO | WO2005072374 A2 | 8/2005 |
| WO | WO2005096759 A2 | 10/2005 |
| WO | WO2006037078 A2 | 4/2006 |
| WO | WO2006039636 A2 | 4/2006 |
| WO | WO2006094988 A2 | 9/2006 |
| WO | WO2007035402 A2 | 3/2007 |
| WO | WO 2007/051307 A2 | 5/2007 |
| WO | WO 2007/101857 A2 | 9/2007 |

OTHER PUBLICATIONS

Morgan, Sarah E. et al. "Surface characterization of rigid rod polymers", Annual Technical Conference—Society of Plastics Engineers (2004), 62nd (vol. 2), pp. 1943-1947 ; 5 pgs.

Beevers A. "New self-reinforcing polymer is stronger and harder than any other", (2004) Plastics Industry News, May 20, 2004, retrieved online via http://www.PWR.com on Aug. 9, 2007—currently retrievable on the Internet URL: http://www.prw.com/subscriber/archshow.html?id=11748&q=Parmax+2004#Szene_1; 2 pgs.

Ogando J. "Unreinforced plastics get stiffer", Design news (Nov. 6, 2006), vol. 61, (16), p. 57, currently retrievable on the Internet: URL: http://www.designnews.com/article/print/4890-Unreinforced_Plastics_Get_Stiffer.php; 3 pgs.

Solvay Advanced Polymers "PrimoSpire™ self-reinforced polyphenylene", 2007, Brochure PR-50497, 20070200; 4 pgs.

Mississippi Polymer Technologies "Parmax® self-reinforced polymers", Brochure, 2 pg. (no publication date).

Solvay Advanced Polymers, "Solvay Advanced Polymers launches Solviva™ Biomaterials available for use in implantable medical devices", Kunstoffe Show press release, Oct. 24, 2007 ; 3 pgs.

Zoller P. et al., "Pressure-Volume-Temperature Properties of Blends of Poly(2,6-dimethyl-1,4-phenylene Ether) with Polystyrene", Journal of Polymer Science : Polymer Physics Edition (1982), 20, pp. 1385-1397, John Wiley & Sons, Inc. ; 13 pgs.

Flory P.J., "Principles of Polymer Chemistry", 1953, Chapter 13, p. 555, Cornell University Press ; 2 pgs.

Weast R.C., "Definitive rules for nomenclature of organic chemistry", CRC Handbook of Chemistry and Physics, 64th edition, (1983-1984), pp. C1-C44, CRC Press Inc., Boca Raton, Florida ; 44 pgs.

Randic M., "Aromaticity of Polycyclic Conjugated Hydrocarbons", Chemical Reviews (2003), vol. 103, pp. 3449-3605, American Chemical Society ; 157 pgs.

Wang Y. et al., "Clinical report of cervical arthroplasty in management of spondylotic myelopathy in Chinese", Journal of Orthopaedic Surgery and Research 2006, 1:13 doi:10.1186/1749-799X-1-13, http://www.josr-online.com/content/1/1/13 ; 6 pgs.

Hyperdictionary,com, "Meaning of prosthetic, prosthesis, dentistry, orthodontic, orthodontics and prosthodontics", http://www.hyperdictionary.com/dictionary/, copyright 2000-2009 ; 6 pgs.

Dijckstra D.J. et al., "Worm-like morphology of semi-rigid substituted poly(p-phenylene)", J. Material Science, 2007, vol. 42, pp. 3810-3815, DOI 10.1007/s10853-006-0426-8, Ed. Springer Science+Business Media, LLC ; 6 pgs.

Schwartz M., "Collaborative research and development (CR&D) Delivery order 0023: Molecular simulation for material design limits", Nov. 2005, 59 pgs.

U.S. Appl. No. 12/676,989, filed Apr. 21, 2010, David B. Thomas et al.

U.S. Appl. No. 12/061,442, filed Apr. 2, 2008, Mohammad Jamal El-Hibri et al.

U.S. Appl. No. 11/850,739, filed Sep. 6, 2007, Nikica Maljkovic et al.

* cited by examiner

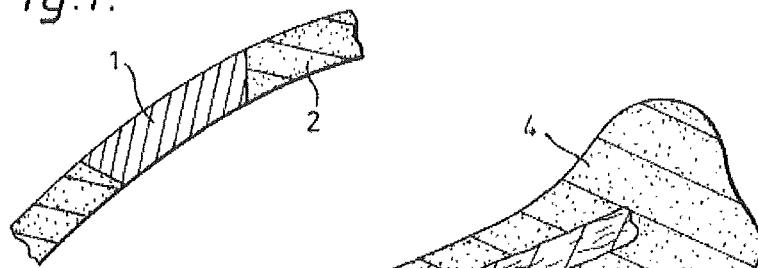
Fig.1.
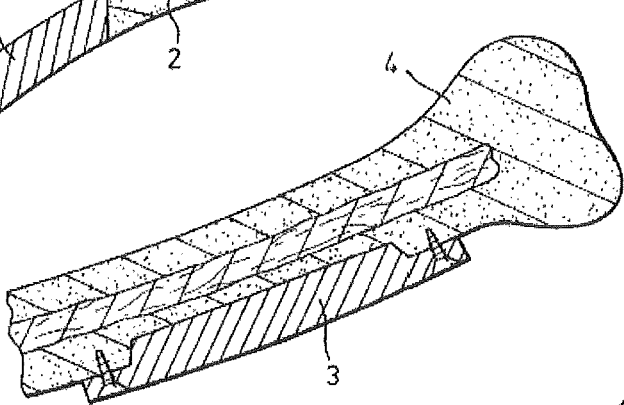
Fig.2.
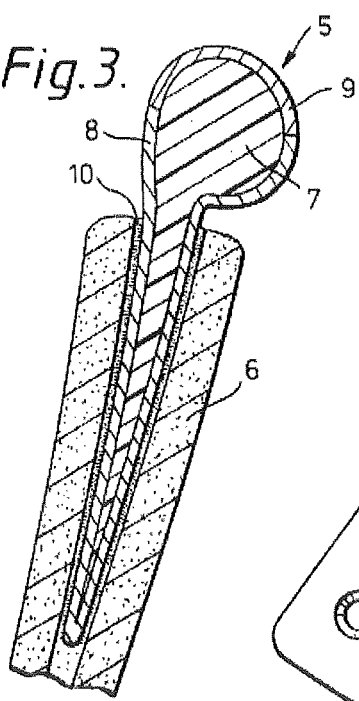
Fig.3.
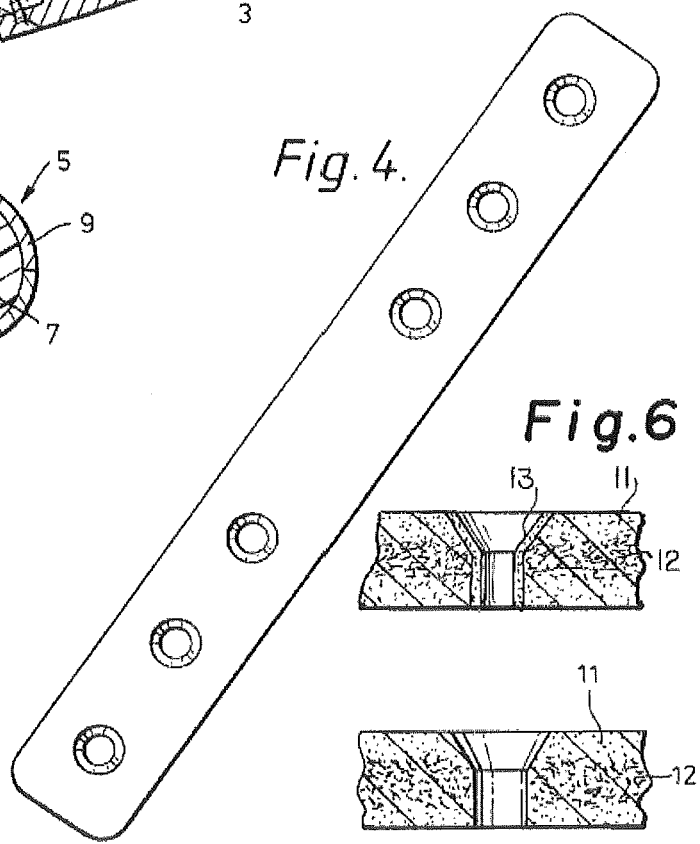
Fig.4.
Fig.6
Fig.5.

PROSTHETIC DEVICES

REFERENCE TO RELATED APPLICATIONS

The present application is a continuation-in-part of PCT application no. PCT/EP2008/061947 and of PCT application no. PCT/EP2008/061948, both filed Sep. 9, 2008 and both claiming the benefit under 35 U.S.C. §119(e) of U.S. provisional application No. 60/971,314 filed Sep. 11, 2007 and of U.S. provisional application No. 60/971,934 filed Sep. 13, 2007, the whole content of all these applications being incorporated herein by reference for all purposes.

FIELD OF THE INVENTION

The present invention is related to a prosthetic device comprising at least one part consisting of a polymer composition comprising at least one polyarylene (P1) and at least one polyarylether selected from the group consisting of poly(aryl ether ketone)s (P2) and poly(aryl ether sulfone)s (P3).

The prosthetic devices of the present invention feature some unexpected advantages because of the compositions of which they are made.

BACKGROUND OF THE INVENTION

Due both to demographic change and to developments in medical science, the number of surgical procedures involving prosthesis implantation is rising rapidly. The more obvious examples of prosthetic devices are hip or knee replacements and false teeth. Other less well-known examples are stents, heart valves, bone screws and plates and spinal fixators.

Prosthesis must be tolerated by the patient and not altered in time. Materials that may be suitable for each type of prosthesis are subjected to precise specifications. Indeed, if the prosthesis is a dental implant or a hip replacement the specifications will be very different. The most important requirements are mechanical properties similar to those of bone to allow the transfer constraints between bone and prosthesis, chemical resistance to corrosion, chemical inertia in relation to the environment and biocompatibility. These properties must be controlled to maintain the integrity of used materials. The human body is an aggressive and corrosive environment mainly because of concentrations of chloride ions (113 mEq/l in blood plasma and 117 mEq/l in the interstitial fluid, which is sufficient to corrode metallic materials) and dissolved oxygen. For dental implants, conditions are even tougher since the saliva contains more sulfur products that make it still more corrosive. The term "biocompatibility" is defined by the Dorland's Medical Dictionary as the quality of not having toxic or injurious effects on biological systems. This encompasses both the material and host responses to an implant. The host response to an implant can be highly complex and is often linked to the material response. It is also dependent on the anatomical position of the implant. For a material to be biocompatible, it should not elicit any adverse host reactions to its presence. Inflammation and encapsulation phenomena may occur when the prosthesis suffer from low biocompatibility.

Typically, prosthetic devices are made of inorganic (metal, alloys, ceramic and glass) and/or polymeric materials.

It is a fact that most pure metals and alloys are chemically unstable in many everyday environments due to their tendency to corrode. In the complex environment of the human body, metals and alloys are subject to electrochemical corrosion mechanisms, with bodily fluids acting as an electrolyte. While alloys such as stainless steel may appear to be highly stable and are widely used for kitchenware, eating utensils and jewelry, there are many situations that can cause severe corrosion of this material, and it is not the best choice for use in prosthetic devices.

Compared to inorganic materials, polymeric materials have certain advantages: they are lightweight, corrosion resistant, they can be directly shaped by molding and offer design freedoms. Over the past 4 years, the price of steel and non-ferrous metals grew faster than polymers and they require also less energy to be implemented. Among various existing polymers, only some of them have been used in the prosthesis industry so far, mainly because of their biocompatibility. Examples of such polymers are polymethyl methacrylate, polystyrene, poly(ether ether ketone).

The Applicant has found that specific polymeric compositions feature surprisingly outstanding properties and in particular a good biocompatibility and impact resistance. These outstanding properties may be useful in certain demanding applications, such as articles used as prosthetic devices.

Polyarylenes, especially polyphenylenes, exhibit some outstanding performance properties, including exceptionally high strength, stiffness, hardness, scratch resistance, friction and wear properties and dimensional stability. Unfortunately, polyarylenes while offering an exceptionally high level of strength and stiffness have some limitations in toughness-related properties, in particular in terms of impact resistance (as typically characterized by standard notched and unnotched Izod tests) and elongation properties. They have also limitations in melt processability due to their high viscosities, and tend to be anisotropic when melt fabricated under high shear such as during injection molding. Also, they have some limitations in chemical resistance.

Poly(aryl ether ketone)s, especially poly(ether ether ketone)s, exhibit also some outstanding properties, including exceptionally high melting point, excellent chemical resistance (including environmental stress cracking resistance) and excellent thermal stability. They have also high strength, stiffness, although somewhat lower than that of polyarylenes, and very good elongation properties. On the other hand, like polyarylenes, they have some limitations in terms of impact resistance.

Poly(aryl ether sulfone)s in general and poly(biphenylether sulfone)s in particular are typically amorphous and do not melt crystallize. Due to their high strength and heat resistance, certain poly(aryl ether sulfone)s may be used in high-stress environments where other polymers may degrade or may otherwise be unsuitable. Poly(aryl ether sulfone)s provide good chemical resistance, toughness, lightness and strength, processability in the melt phase including injection molding and extrusion; and ease of colorability.

Polymer blends have been widely taught and employed in the art. As broad as this statement may be, the blending of polymers remains an empirical art and the selection of polymers for a blend giving special properties is, in the main, an Edisonian-like choice. Certain attributes of polymer blends are more unique than others. The more unique attributes when found in a blend tend to be unanticipated properties. According to Zoller and Hoehn, Journal of Polymer Science, Polymer Physics Edition, vol. 20, pp. 1385-1397 (1982): "Blending of polymers is a useful technique to obtain properties in thermoplastic materials not readily achieved in a single polymer. Virtually all technologically important properties can be improved in this way, some of the more important ones being flow properties, mechanical properties (especially impact strength), thermal stability, and price ( . . . ). Ultimately, the goal of such modeling and correlation studies should be the prediction of blend properties from the properties of the pure components alone. We are certainly very far from achieving this goal." Moreover, in the field of miscibility or compatibility of polymer blends, the art has found predictability to be unattainable, even though considerable work on the matter has been done. According to authorities: "It is well known that, regarding the mixing of thermoplastic polymers, incompatibility is the rule and miscibility and even partial miscibility is the exception. Since most thermoplastic polymers are immiscible in other thermoplastic polymers, the discovery of a homogeneous mixture or partially miscible mixture of two or more thermoplastic polymers is, indeed, inherently unpredictable with any degree of certainty"; for example, see P. J. Flory, Principles of Polymer Chemistry, Cornell University Press, 1953, Chapter 13, page 555.

U.S. Pat. No. 4,662,887 describes a high modulus prosthetic device made of poly(ether ether ketone).

U.S. 2007111165 describes a prosthetic dental device made of a thermoplastic polymer including a poly(aryl ketone), such as poly(ether ether ketone) (PEEK), polymethylmethacrylate (PMMA), poly(aryl ether ketone) (PAEK), poly(ether ketone) (PEK), poly(ether ketone ether ketone ketone) (PEKEKK), poly(ether ketone ketone) (PEKK), and/or polyetherimide (PEI), polysulfone (PSU), and polyphenylsulfone (PPSU).

All materials used in the prior art prosthetic devices still suffer from a limited impact resistance, which is a key property for such application where such materials are submitted to various and harsh conditions.

There remains thus a strong need for a prosthetic device presenting a superior balance of properties, including part or preferably all of the following ones:
  very high strength;
  very high stiffness;
  good elongation properties;
  good melt processability (in particular, good injection moldability);
  high chemical resistance;
  good biocompatibility;
  outstanding impact resistance, as possibly characterized by a standard no-notch IZOD test (ASTM D-4810).

In fact, there is a specific need to improve the mechanical properties of the existing prosthetic devices and in particular their impact resistance while at least maintaining their biocompatibility.

BRIEF DESCRIPTION OF THE FIGURES

Illustrated in sectional view in the drawings are, in

FIG. 1, a cranial plate 1 in situ within an aperture cut into the skull 2; in FIG. 2 an insert 3 in a long bone 4 from which part of the bone had been removed; and in FIG. 3 a femur head replacement 5 in situ within a femur 6. This last device comprises a core component 7 of a cement composition as described in European Patent Specification No. 21682 and comprising a core component 7 and/or a surface coating 8 of a polymer composition comprising at least one polyarylene (P1) and at least one poly(aryl ether ketone)s (P2) and/or poly(aryl ether sulfone)s (P3) a bearing surface 9 of titanium and a fibrous surface layer 10.

Figure 7:
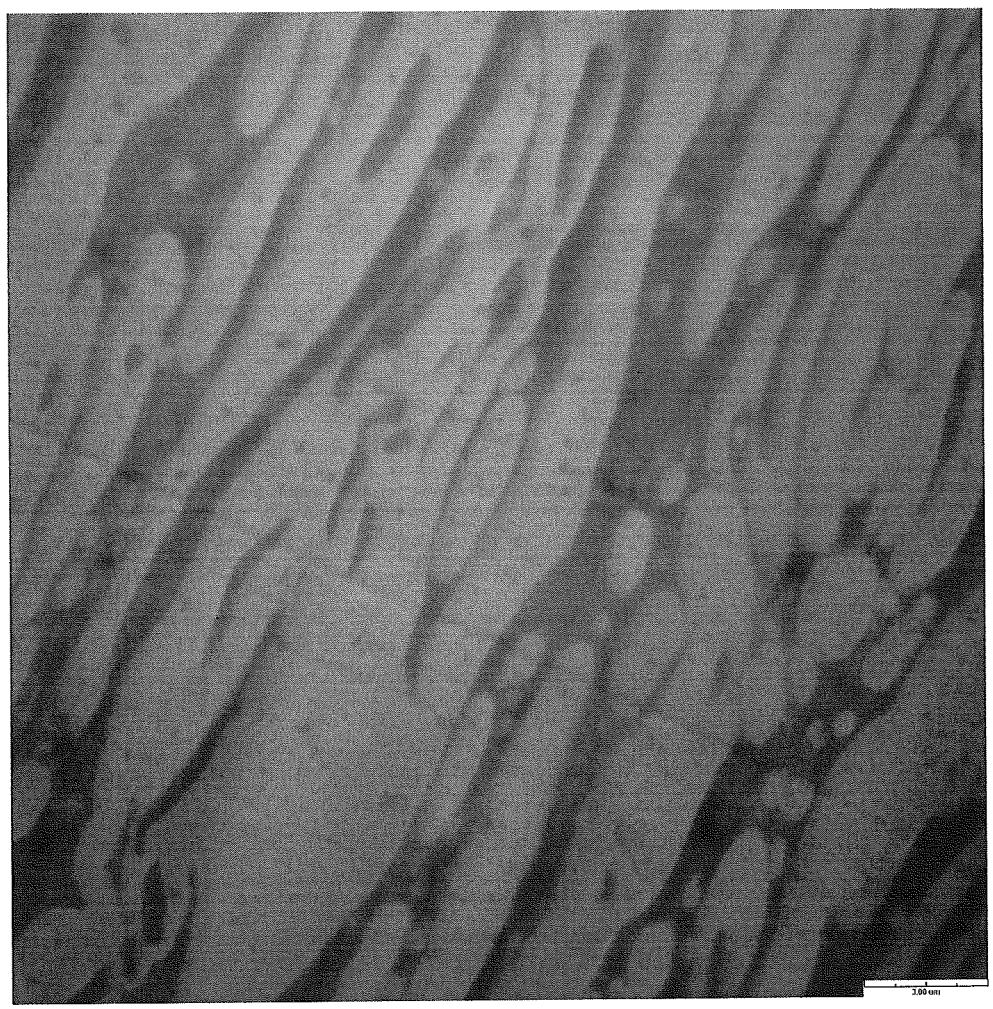

A bone plate shown in perspective in

FIG. 4 is shown also in enlarged section in

FIG. 5, to illustrate the use of a polymer composition comprising at least one polyarylene (P1) and at least one poly(aryl ether ketone)s (P2) and/or poly(aryl ether sulfone)s (P3) outer coating 11 upon a core region comprising a composite of carbon fibre with a polymer composition comprising at least one polyarylene (P1) and at least one poly(aryl ether ketone)s (P2) and/or poly(aryl ether sulfone)s (P3) 12.

FIG. 6 shows the presence of polymer composition comprising at least one polyarylene (P1) and at least one poly(aryl ether ketone)s (P2) and/or poly(aryl ether sulfone)s (P3) 13 also after refilling of the screw holes and redrilling.

FIG. 7 is a TEM photomicrograph showing the morphology of a blend composed of 50 parts by weight of PRIMOSPIRE® PR-250 polyphenylene and of 50 parts by weight of VICTREX® 150 P poly(ether ether ketone), which is used for manufacturing the prosthetic device in accordance with the present invention.

DETAILED DESCRIPTION OF THE INVENTION

The present invention is related to a prosthetic device comprising at least one part consisting of a polymer composition comprising at least one polyarylene (P1) and at least one polyarylether selected from the group consisting of poly(aryl ether ketone)s (P2) and poly(aryl ether sulfone)s (P3).

The Prosthetic Device

To the purposes of the invention, the term "prosthetic device" is intended to denote an artificial device which is made to replace and act as a missing biological structure. Prosthetic devices may have structural features which make them suitable to act as reinforcement or replacement of a missing or defective animal or human body part, e.g. a bone implant. Prosthetic devices of many shapes, configurations and properties are commonly employed within the living body. They can be used to replace parts lost by injury (traumatic or chirurgical) or missing from birth (congenital) or to supplement defective body parts.

For the sake of clarity, the term "part of a prosthetic device" is intended to denote a piece or portion which is combined with others to make up the whole prosthetic device. The external coating of a prosthetic device falls thus within this scope.

The prosthetic device of the present invention may be composed of at least one part consisting of a polymer composition comprising at least one polyarylene (P1) and at least one polyarylether selected from the group consisting of poly(aryl ether ketone)s (P2) and poly(aryl ether sulfone)s (P3). Alternatively, the prosthetic device of the present invention may further comprise at least one part consisting of a material other than the above polymer composition.

The prosthetic device of the present invention may comprise additional parts. Additional parts are intended to denote parts of the prosthetic devices which do not aim to replace a part of the body as such, but perform a supplementary function. For instance, it may comprise metal inserts, structural reinforcements, radio-opaque inserts, moving motor-driven assemblies, electronic devices, controlling units and the like.

The prosthetic device according to the present invention may be an orthopaedic prosthesis for building and/or repairing and/or improving surface properties of skeletal bones and joints such as, but not limited to ligaments, tendons, cartilage, bones, hip joints, knee prosthesis, spinal disc orthoprosthesis.

Orthopaedic prostheses comprise manufactured replacements for the ends and articulating surfaces of the bones of the skeleton. Such prostheses are generally implanted to repair or reconstruct all or part of an articulating skeletal joint that is functioning abnormally due to disease, trauma or congenital defect. Other forms of implantable orthopaedic prostheses, beyond providing manufactured replacements for the ends and articulating surfaces of the bones of the skeletal joints, also provide manufactured replacements for portions of the bones distant from the articulating surface. These other forms may be used in cases of abnormally extensive atrophy or resorption of bone in the vicinity of the articulating surface or prior implant, or in cases where an extensive amount of bone is to be intentionally resected to treat oncological or other diseases of the bone. Because the natural bony areas to which ligaments, tendons and other soft tissues attach are often lost to such extensive resections of the bone, implantable orthopaedic implants designed for such cases often include means for attaching bone and/or soft tissue directly to the implant. Generally such means also provide an initial mechanical attachment, supplemented by later ingrowth and ongrowth of the bone and soft tissue to the prosthesis.

Example of such prosthetic devices are described in many patent references, such as in U.S. Pat. No. 4,164,794A, U.S. Pat. No. 4,351,069A, U.S. Pat. No. 4,662,887A, U.S. Pat. No. 5,064,439A, U.S. Pat. No. 5,219,363A, U.S. Pat. No. 5,397,365A, U.S. Pat. No. 5,443,512A, U.S. Pat. No. 5,176, 710A, U.S. Pat. No. 5,181,930A, GB 2,259,253A1, U.S. Pat. No. 5,370,696A, U.S. Pat. No. 5,236,457A, EP 0598450A1, U.S. Pat. No. 5,872,159A, EP 0761242A1, U.S. Pat. No. 5,782,930A, U.S. Pat. No. 6,602,293B, GB 2,319,962A1, DE 19728131A1, DE 19823737A1, US 2002107577A, US 2002111691A, WO 02070031A1, US 2002099449A, US 2002115742A, US 2002120336A, US2004158324A, WO 02071959A1, US 2002173850A, US 2003004563A, US 2003135275A, US 2003195327A, US 2004059356A, DE 10256345C1, BE 1015402, US 2004249471A, CN 1582860A, US 2005228498A, US 2005136764A, WO 05096759A2, CN 1593356A, WO 06039636A2, US 2006116774A, US 2006200245A, US 2006241759A, US 2006247638A, WO 07051307A2 and EP 1813292A, the whole content of all of them being herein incorporated by reference.

For example, the prosthetic device of the present invention may be selected from the group consisting of:
 orthopaedic prosthesis such as ligaments, tendons, cartilage, bones, hip joints, knee prosthesis, spinal disc orthoprosthesis;
 dental structures such as dentures, partial dentures;
 prosthetic structures for other body parts, such as prosthetic devices that serve as artificial body parts including limbs, eyes, implants, included cosmetic implants, hearing aids, and the like, such as spectacle frames;
 fixed prosthetic anatomical devices such as caps, crowns and other non-dental anatomical replacement structures.

The Polyarylene (P1)

For the purpose of the present invention, an arylene group is a hydrocarbon divalent group consisting of one core composed of one benzenic ring or of a plurality of benzenic rings fused together by sharing two or more neighboring ring carbon atoms, and of two ends.

Non limitative examples of arylene groups are phenylenes, naphthylenes, anthrylenes, phenanthrylenes, tetracenylenes, triphenylylenes, pyrenylenes, and perylenylenes. The arylene groups (especially the numbering of the ring carbon atoms) were named in accordance with the recommendations of the CRC Handbook of Chemistry and Physics, $64^{th}$ edition, pages C1-C44, especially p. C11-C12.

Arylene groups present usually a certain level of aromaticity; for this reason, they are often reported as "aromatic" groups. The level of aromaticity of the arylene groups depends on the nature of the arylene group; as thoroughly explained in Chem. Rev. 2003, 103, 3449-3605, "Aromaticity of Polycyclic Conjugated Hydrocarbons", the level of aromaticity of a polycyclic aromatic hydrocarbon can be notably quantified by the "index of benzene character" B, as defined on p. 3531 of the same paper; values of B for a large set of polycyclic aromatic hydrocarbon are reported on table 40, same page.

An end of an arylene group is a free electron of a carbon atom contained in a (or the) benzenic ring of the arylene group, wherein an hydrogen atom linked to said carbon atom has been removed. Each end of an arylene group is capable of forming a linkage with another chemical group. An end of an arylene group, or more precisely the linkage capable of being formed by said end, can be characterized by a direction and by a sense; to the purpose of the present invention, the sense of the end of an arylene group is defined as going from the inside of the core of the arylene group to the outside of said core. As concerns more precisely arylene groups the ends of which have the same direction, such ends can be either of the same or opposite sense; also, their ends can be in the straight foregoing of each other, or not (otherwise said, they can be disjoint).

A polyarylene is intended to denote a polymer, other than a poly(aryl ether ketone) as defined below, of which more than 25 wt. % of the recurring units are recurring units (R1) of one or more formulae consisting of an optionally substituted arylene group, provided said optionally substituted arylene group is linked by each of its two ends to two other optionally substituted arylene groups via a direct C—C linkage. That the optionally substituted arylene group is linked by each of its two ends to two other optionally substituted arylene groups via a direct C—C linkage, is an essential feature of the recurring units (R1); thus, an arylene recurring unit which is linked by at least one of its two ends to a group other than an arylene group such as phenylene recurring units $\phi_1$, $\phi_2$ and $\phi_{2'}$ below:

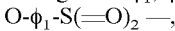
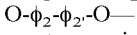

are not recurring units (R1) in the sense of the present invention.

The arylene groups of which the recurring units (R1) consist can be unsubstituted. Alternatively, they can be substituted by at least one monovalent substituting group.

The monovalent substituting group is usually not polymeric in nature; its molecular weight is preferably below 500, more preferably below 300, still more preferably below 200 and most preferably below 150.

The monovalent substituting group is advantageously a solubilizing group. A solubilizing group is one increasing the solubility of the polyarylene (P1) in at least one organic solvent, in particular in at least one of dimethylformamide, N-methylpyrrolidinone, hexamethylphosphoric triamide, benzene, tetrahydrofuran and dimethoxyethane, which can be used as solvents during the synthesis of the polyarylene (P1) by a solution polymerization process.

The monovalent substituting group is also advantageously a group which increases the fusibility of the polyarylene (P1), i.e. it lowers its glass transition temperature and its melt viscosity, so as to desirably make the polyarylene (P1) suitable for thermoprocessing.

Preferably, the monovalent substituting group is chosen from:
hydrocarbyls such as alkyls, aryls, alkylaryls and aralkyls;
halogenos such as —Cl, —Br, —F and —I;
hydrocarbyl groups partially or completely substituted by at least one halogen atom such as halogenoalkyls, halogenoaryls, halogenoalkylaryls and halogenoaralkyls;
hydroxyl;
hydrocarbyl groups substituted by at least one hydroxyl group, such as hydroxyalkyls, hydroxyaryls, hydroxyalkylaryls and hydroxyaralkyls;
hydrocarbyloxys [—O—R, where R is a hydrocarbyl group], such as alkoxys, aryloxys, alkylaryloxys and aralkyloxys;
amino (—$NH_2$);
hydrocarbyl groups substituted by at least one amino group, such as aminoalkyls and aminoaryls;
hydrocarbylamines [—NHR or —$NR_2$, where R is a hydrocarbyl group] such as alkylamines and arylamines;
carboxylic acids and their metal or ammonium salts, carboxylic acid halides, carboxylic anhydrides;
hydrocarbyl groups substituted by at least one of carboxylic acids, metals or ammonium salts thereof, carboxylic acid halides and carboxylic anhydrides, such as —R—C(=O)OH where R is an alkyl or an aryl group;
hydrocarbylesters [—C(=O)OR or —O—C(=O)R, where R is a hydrocarbyl group] such as alkylesters, arylesters, alkylarylesters and aralkylesters;
amido [—C(=O)$NH_2$];
hydrocarbyl groups substituted by at least one amido group;
hydrocarbylamide monoesters [—C(=O)NHR or —NH—C(=O)—R, where R is a hydrocarbyl group], such as alkylamides, arylamides, alkylarylamides and aralkylamides, and hydrocarbylamide diesters [—C(=O)$NR_2$ or —N—C(=O)$R_2$, where R are a hydrocarbyl groups], such as dialkylamides and diarylamides;
sulfinic acid (—$SO_2H$), sulfonic acid (—$SO_3H$), their metal or ammonium salts,
hydrocarbylsulfones [—S(=O)$_2$—R, where R is the hydrocarbyl group], such as alkylsulfones, arylsulfones, alkylarylsulfones, aralkylsulfones;
aldehyde [—C(=O)H] and haloformyls [—C(=O)X, wherein X is a halogen atom];
hydrocarbylketones [—C(=O)—R, where R is a hydrocarbyl group], such as alkylketones, arylketones, alkylarylketones and aralkylketones;
hydrocarbyloxyhydrocarbylketones [—C(=O)—$R^1$—O—$R^2$, where $R^1$ is a divalent hydrocarbon group such as an alkylene, an arylene, an alkylarylene or an aralkylene, preferably a $C_1$-$C_{18}$ alkylene, a phenylene, a phenylene group substituted by at least one alkyl group, or an alkylene group substituted by at least one phenyl group; and $R^2$ is a hydrocarbyl group, such as an alkyl, aryl, alkylaryl or aralkyl group], such as alkyloxyalkylketones, alkyloxyarylketones, alkyloxyalkylarylketones, alkyloxyaralkylketones, aryloxyalkylketones, aryloxyarylketones, aryloxyalkylarylketones and aryloxyaralkylketones;
any of the above groups comprising at least one hydrocarbyl group or a divalent hydrocarbon group $R^1$, wherein said hydrocarbyl group or said $R^1$ is itself substituted by at least one of the above listed monovalent substituting groups, e.g. an arylketone —C(=O)—R, where R is an aryl group substituted by one hydroxyl group;

where:
the hydrocarbyl groups contain preferably from 1 and 30 carbon atoms, more preferably from 1 to 12 carbon atoms and still more preferably from 1 to 6 carbon atoms;
the alkyl groups contain preferably from 1 to 18 carbon atoms, and more preferably from 1 to 6 carbon atoms; very preferably, they are chosen from methyl, ethyl, n-propyl, isopropyl, n-butyl, isobutyl and tert-butyl;
the aryl groups are defined as monovalent groups consisting of one end and one core composed of one benzenic ring (such the phenyl group) or of a plurality of benzenic rings directly linked to each other via a carbon-carbon linkage (such as the biphenyl group) or fused together by sharing two or more neighboring ring carbon atoms (such as the naphthyl groups), and wherein the ring carbon atoms are possibly substituted by at least one nitrogen, oxygen or sulfur atom; preferably, in the aryl groups, no ring carbon atom is substituted;
the aryl groups contain preferably from 6 to 30 carbon atoms; more preferably, they are phenyl groups;
the alkyl group which is contained in the alkylaryl groups meets the preferences of the alkyl groups as above expressed;
the aryl group which is contained in the aralkyl groups meets the preferences of the aryl groups as above expressed.

More preferably, the monovalent substituting group is chosen from hydrocarbylketones [—C(=O)—R, where R is a hydrocarbyl group] and hydrocarbyloxyhydrocarbylketones [—C(=O)—$R^1$—O—$R^2$, where $R^1$ is a divalent hydrocarbon group and $R^2$ is a hydrocarbyl group], said hydrocarbylketones and hydrocarbyloxyhydrocarbylketones being unsubstituted or substituted by at least one of the above listed monovalent substituting groups.

Still more preferably, the monovalent substituting group is chosen from arylketones and aryloxyarylketones, said arylketones and aryloxyarylketones being unsubstituted or substituted by at least one of the above listed monovalent substituting groups.

Most preferably, the monovalent substituting group is an (unsubstituted) arylketone, in particular it is phenylketone [—C(=O)-phenyl].

The core of the optionally substituted arylene group of the recurring units (R1) is composed of preferably at most 3, more preferably at most 2, and still more preferably at most one benzenic ring. Then, when the core of the optionally substituted arylene group of the recurring units (R1) is composed of one benzenic ring, the recurring units (R1) are of one or more formulae consisting of an optionally substituted phenylene group, provided said optionally substituted phenylene group is linked by each of its two ends to two other optionally substituted arylene groups via a direct C—C linkage.

As above explained, the optionally substituted arylene group of the recurring units (R1) is linked by each of its two ends to two other optionally substituted arylene groups via a direct C—C linkage. Preferably, it is linked by each of its two ends to two other optionally substituted phenylene groups via a direct C—C linkage.

As also above explained, both ends of the optionally substituted arylene group of the recurring units (R1) can be characterized notably by a direction and by a sense.

A first set of recurring units suitable as recurring units (R1) is composed of optionally substituted arylene groups, the ends of which have the same direction, are of opposite sense, and are in the straight foregoing of each other

[hereafter, recurring units (R1-a)].

Non limitative examples of such optionally substituted arylene groups include:

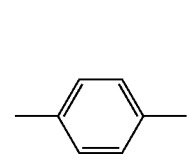 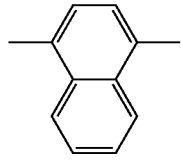

1,4-phenylene (also named p-phenylene)     1,4-naphtylene

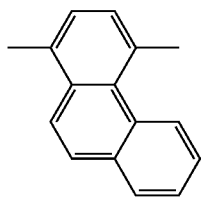

and

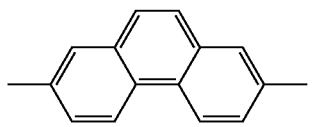

1,4-phenanthrylene and 2,7-phenanthrylene

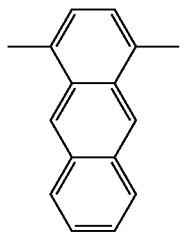 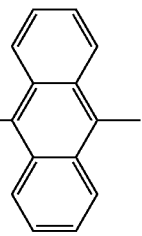

and 1,4-anthrylene and 9,10-anthrylene

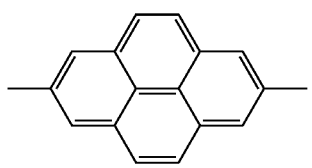

2,7-pyrenylene

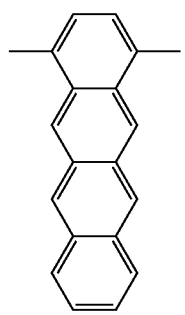 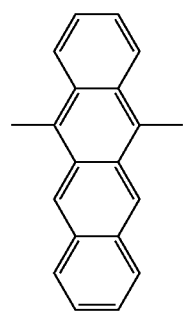

and 1,4-naphthacenylene and 5,12-naphthacenylene

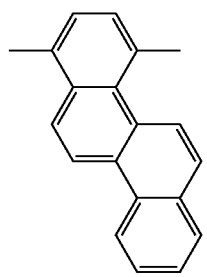

1,4-chrysenylene

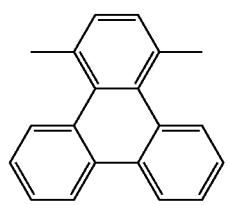

and

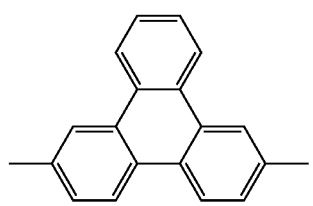

1,4-triphenylylene and 2,7-triphenylylene

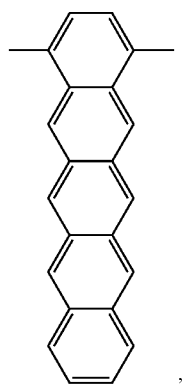 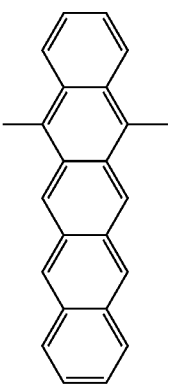

, and

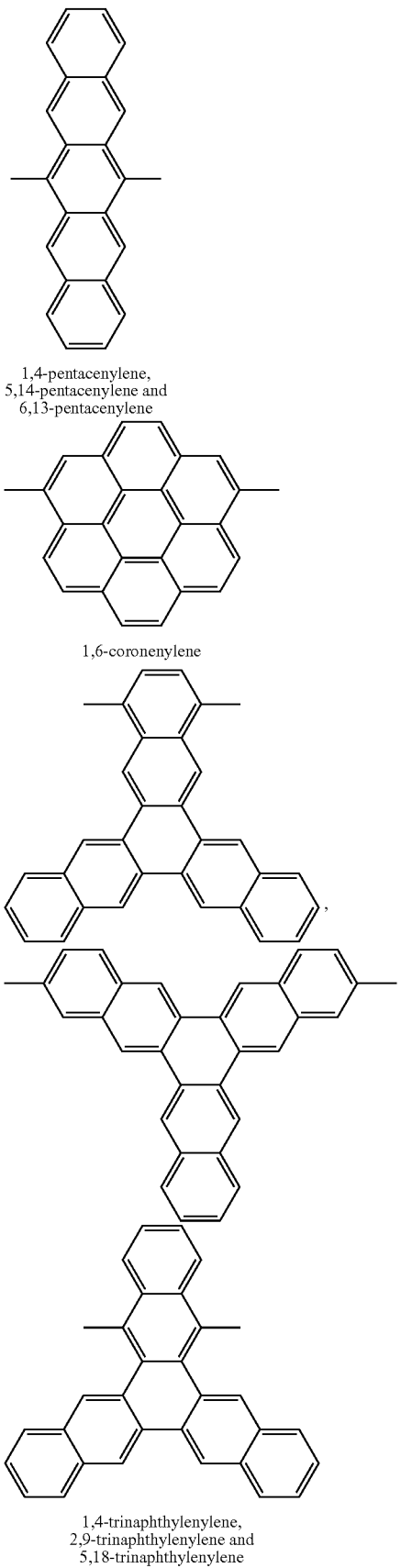

1,4-pentacenylene, 5,14-pentacenylene and 6,13-pentacenylene 1,6-coronenylene 1,4-trinaphthylenylene, 2,9-trinaphthylenylene and 5,18-trinaphthylenylene and any of these groups substituted by at least one monovalent substituting group, as above defined, in particular by a phenylketone group.

Good results are obtained when recurring units (R1-a) are optionally substituted p-phenylenes.

Recurring units (R1-a), when contained in the polyarylene (P1), result in straight polymer chains exhibiting an outstanding rigidity. For this reason, such polyarylenes (P1) are commonly referred to as "rigid-rod polymers".

A second set of recurring units suitable as recurring (R1) is composed of optionally substituted arylene groups, the ends of which

- either have a different direction, forming thus together an angle between 0 and 180°, said angle being possibly acute or obtuse,
- or have the same direction and the same sense,
- or have the same direction, are of opposite sense and are disjoint (i.e. not in the straight foregoing of each other)

[globally hereafter referred to as recurring units (R1-b)].

Then, a first subset of recurring units (R1-b) suitable as recurring units (R1) is composed of optionally substituted arylene groups, the ends of which have a different direction, forming together an acute angle [recurring units (R1-b1)]. Non limitative examples of optionally substituted arylene groups the ends of which have a direction different from each other, include:

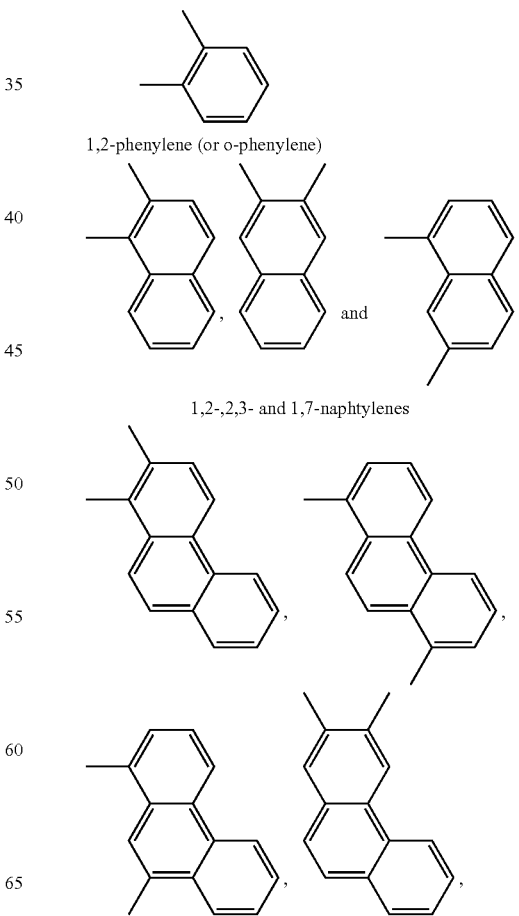

1,2-phenylene (or o-phenylene)

1,2-, 2,3- and 1,7-naphtylenes and

-continued

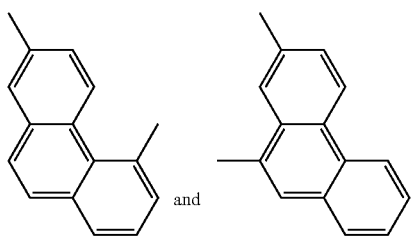

1,2-, 1,8-, 1,9-, 2,3-, 2,5- and 2,10-phenanthrylenes

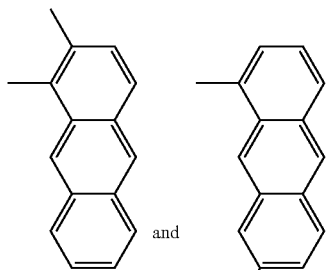

1,2- and 1,7-anthrylenes and any of these groups substituted by at least one monovalent substituting group, as above defined, in particular by a phenylketone group.

A second subset of recurring units (R1-b) suitable as recurring units (R1) is composed of optionally substituted arylene groups, the ends of which have a different direction, forming together an obtuse angle [recurring units (R1-b2)]. Non limitative examples of optionally substituted arylene groups the ends of which have a direction different from each other, include:

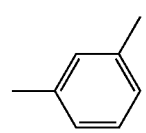

1,3-phenylene (or m-phenylene)

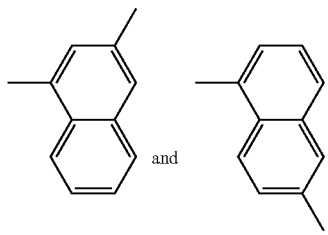

1,3- and 1,6-naphtylenes

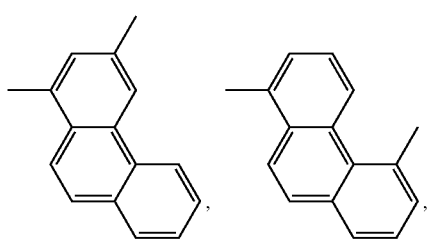

-continued

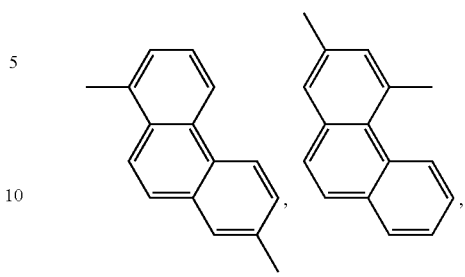

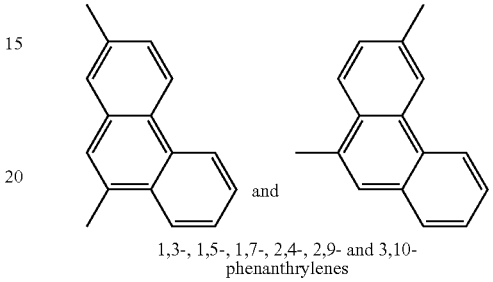

1,3-, 1,5-, 1,7-, 2,4-, 2,9- and 3,10-phenanthrylenes

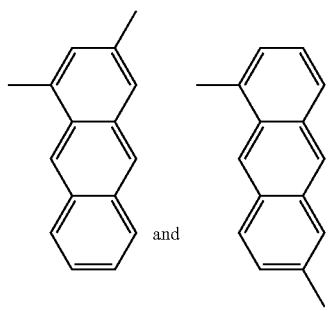

1,3- and 1,6-anthrylenes and any of these groups substituted by at least one monovalent substituting group, as above defined, in particular by a phenylketone group.

A third subset of recurring units (R1-b) is composed of optionally substituted arylene groups, the ends of which have the same direction and the same sense [recurring units (R1-b3)]. Non limitative examples of optionally substituted arylene groups the ends of which the same direction and the same sense include:

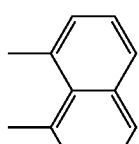

1,8-naphthylene

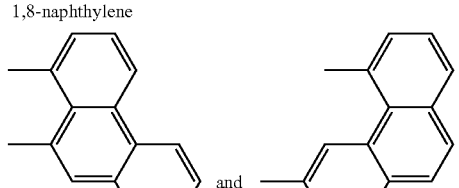

1,10- and 3,5-phenanthrylenes

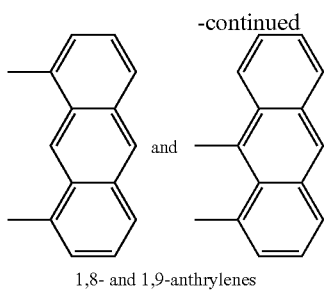

1,8- and 1,9-anthrylenes and any of these groups substituted by at least one monovalent substituting group, as above defined, in particular by a phenylketone group.

A fourth subset of recurring units (R1-b) is composed of optionally substituted arylene groups, the ends of which have the same direction, are of opposite sense and are disjoint [recurring units (R1-b4)]. Non limitative examples of such optionally substituted arylene groups include:

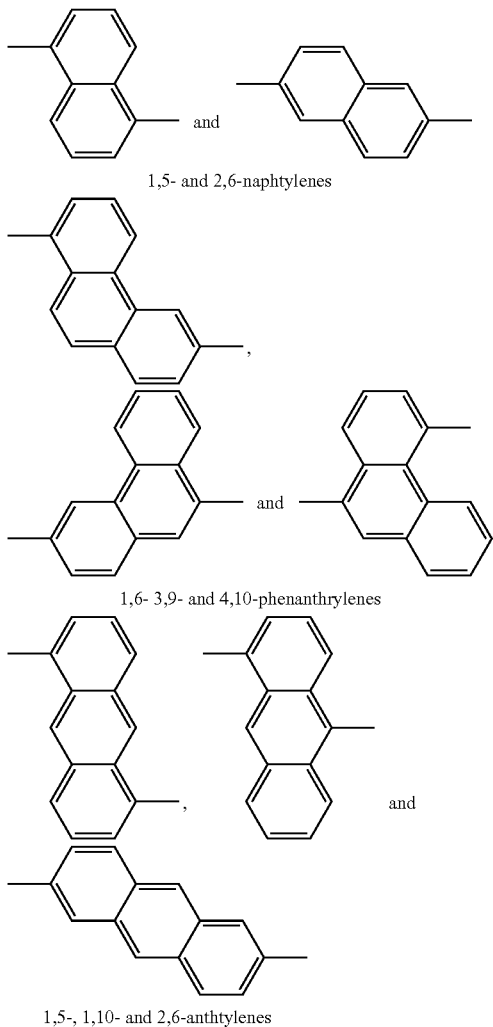

and any of these groups substituted by at least one monovalent substituting group, as above defined, in particular by a phenylketone group. Preferably, recurring units (R1-b) are chosen from recurring units (R1-b1), recurring units (R1-b2) and recurring units (R1-b4). More preferably, recurring units (R1-b) are chosen from recurring units (R1-b1) and recurring units (R1-b2). Still more preferably, recurring units (R1-b) are chosen from recurring units (R1-b1). Good results are obtained when recurring units (R1-b) are optionally substituted m-phenylenes.

Recurring units (R1-b), when contained in the polyarylene (P1), result in more or less kinked polymer chains, exhibiting a higher solubility and fusibility than straight polymer chains. For this reason, such polyarylenes (P1) are commonly referred to as "kinked polymers".

Recurring units (R1) are preferably chosen from:
recurring units (R1-a) which are substituted by at least one monovalent substituting group [choice (A)]; and
mixes of recurring units (R1-a), which can be substituted or not by at least one monovalent substituting group, with recurring units (R1-b), which can be substituted or not by at least one monovalent substituting group [choice (B)].

Choice (B) is generally more preferred than choice A.

Choice (A)

Recurring units of choice (A) are recurring units (R1-a) which are substituted by at least one monovalent substituting group.

Said recurring units are preferably p-phenylenes substituted by at least one monovalent substituting group.

Very preferably, they are p-phenylenes substituted by at least one monovalent substituting group chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed.

Still more preferably, they are p-phenylenes substituted by at least one monovalent substituting group chosen from arylketones and aryloxyarylketones, said arylketones and aryloxyarylketones being unsubstituted or substituted by at least one monovalent substituting group as those above listed.

Most preferably, they are p-phenylenes substituted by an arylketone group, in particular by the phenylketone group.

Choice (B)

Recurring units of choice (B) are a mix of recurring units (R1-a), which can be substituted or not by at least one monovalent substituting group, with recurring units (R1-b), which can be substituted or not by at least one monovalent substituting group. When such a mix of recurring units is contained in the polyarylene (P1), said polyarylene (P1) is commonly referred to as "a kinked rigid-rod polymer".

The recurring units of choice (B) are preferably a mix (MB) of recurring units (R1-a) chosen from optionally substituted p-phenylenes, with recurring units (R1-b) chosen from (i) optionally substituted m-phenylenes and (ii) mixes of optionally substituted m-phenylenes with optionally substituted o-phenylenes.

The recurring units (R1-a) of the mix (MB) are preferably p-phenylene units substituted by at least one substituting group. More preferably, the recurring units (R1-a) of the mix (MB) are p-phenylenes substituted by at least one monovalent substituting group chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed. Still more preferably, the recurring units (R1-a) of the mix (MB) are p-phenylenes substituted by at least one monovalent substituting group chosen from arylketones and aryloxyarylketones, said arylketones and aryloxyarylketones being unsubstituted or substituted by at least one monovalent substituting group as those above listed. Most preferably, they are p-phenylenes substituted by an arylketone group, in particular by the phenylketone group.

Essentially all, if not all, the recurring units (R1-b) of the mix (MB) are m-phenylene units optionally substituted by at least one substituting group. More preferably, essentially all, if not all, the recurring units (R1-b) of the mix (MB) are m-phenylene units which are optionally substituted by at least one monovalent substituting group chosen from hydrocarbylketones [—C(═O)—R, where R is a hydrocarbyl group] and hydrocarbyloxyhydrocarbylketones [—C(═O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed. Still more preferably, essentially all, if not all, the recurring units (R1-b) of the mix (MB) are unsubstituted m-phenylene units. Most preferably, all the recurring units (R1-b) are m-phenylene units.

In the mix (MB), the mole ratio of the recurring units (R1-b), based on the total number of moles of the recurring units (R1-a) and (R1-b), is usually of at least 1%, preferably at least 5%, more preferably at least 20%, still more preferably at least 30% and most preferably at least 40%. On the other hand, in the mix (MB), the mole ratio of the recurring units (R1-b), based on the total number of moles of the recurring units (R1-a) and (R1-b), is usually of at most 99%, preferably at most 95%, more preferably at most 80%, still more preferably at most 70% and most preferably at most 60%.

Good results are obtained when the recurring units of choice (B) are a mix of p-phenylene substituted by a phenylketone group with unsubstituted m-phenylene, in a mole ratio of about 50:50.

The polyarylene (P1) may be notably a homopolymer, a random, alternating or block copolymer.

Optionally, the polyarylene (P1) may further comprise recurring units (R1*), different from recurring units (R1).

Recurring units (R1*) may contain or not at least one strong divalent electron withdrawing group linked on each of its ends to an arylene group. Non limitative examples of recurring units (R1*) free of such strong divalent electron withdrawing group are:

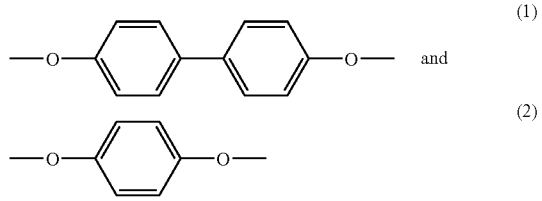

Recurring units (R1*) contain preferably at least one strong divalent electron withdrawing group linked on each of its ends to an arylene group, in particular a p-phenylene group. The divalent electron withdrawing group is preferably chosen from the sulfone group [—S(═O)$_2$—], the carbonyl group [—C(═O)—], the vinylene group [—CH═CH—], the sulfoxide group [—S(═O)—], the azo group [—N═N—], saturated fluorocarbon groups like —C(CF$_3$)$_2$—, organic phosphine oxide groups [—P(═O) (═R$_h$)—, where R$_h$ is a hydrocarbyl group] and the ethylidene group [—C (═CA$_2$)-, where A can be hydrogen or halogen]. More preferably, the divalent electron withdrawing group is chosen from the sulfone group and the carbonyl group. Still more preferably, recurring units (R1*) are chosen from:

(i) recurring units of formula

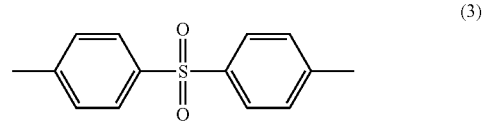

(ii) recurring units of formula

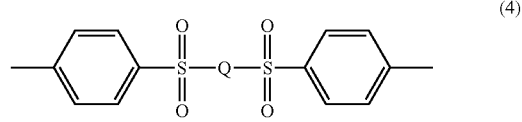

wherein Q is a group chosen from

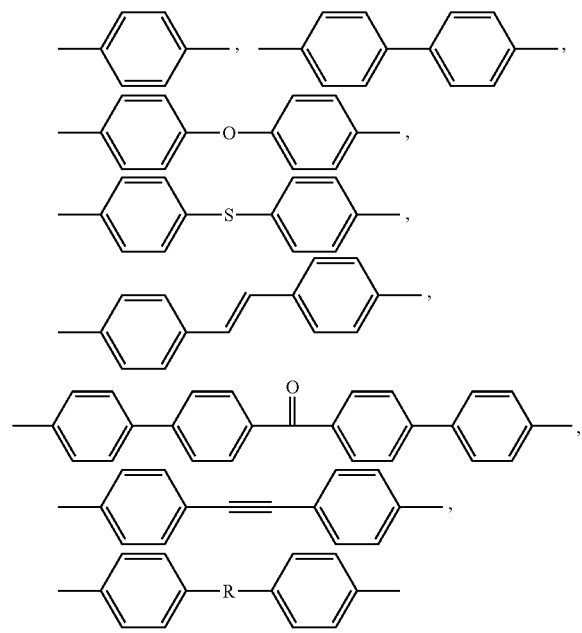

with R being:

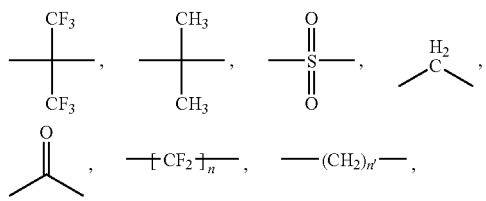

with n being an integer from 1 to 6 and n' being an integer from 2 to 6, Q being preferably chosen from

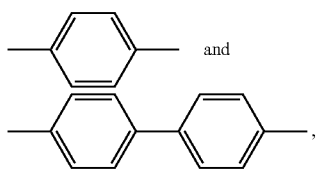

and (iii) recurring units of formula

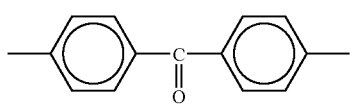

(5)

(iv) recurring units of formula

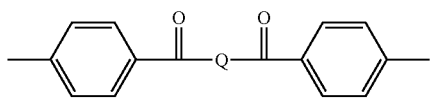

(6)

Preferably more than 25 wt. %, more preferably more than 50 wt. %, and still more preferably more than 90 wt. % of the recurring units of the polyarylene (P1) are recurring units (R1). Most preferably, essentially all, if not all, the recurring units of the polyarylene (P1) are recurring units (R1).

Excellent results are obtained when the polyarylene (P1) is a polyphenylene copolymer, essentially all, if not all, the recurring units of which consisted of a mix of p-phenylene substituted by a phenylketone group with unsubstituted m-phenylene in a mole ratio p-phenylene:m-phenylene of from 5:95 to 95:5, preferably of from 70:30 to 30:70, more preferably of from 60:40 to 40:60, and still more preferably of about 50:50. Such a polyphenylene copolymer is commercially available from Solvay Advanced Polymers, L.L.C. as PRIMOSPIRE® PR-250 polyphenylene, formerly known as PARMAX® 1500. It is also commercially available from Solvay Advanced Polymers, L.L.C. as PRONIVA™ polyphenylene; PRONIVA™ polyphenylene forms part of a new family of engineering polymers launched at the Kunstoffe-Show on Oct. 24, 2007, collectively named SOLVIVA™ Biomaterials, which are offered for use in particular in implantable medical devices. It goes without saying that PRONIVA™ polyphenylene, like any other SOLVIVA™ Biomaterial, is manufactured by carefully validated processes, is subject to enhanced controls to provide product traceability, and is tested in an accredited lab.

Excellent results are also obtained when the polyarylene (P1) is a polyphenylene copolymer, essentially all, if not all, the recurring units of which consisted of a mix of p-phenylene substituted by a phenylketone group with unsubstituted m-phenylene in a mole ratio p-phenylene:m-phenylene of from 75:25 to 99.0:1.0, preferably of from 79:21 to 95:5, more preferably of from 82:18 to 90:10, and still more preferably of about 85:15. Such a kinked rigid-rod polyphenylene copolymer is commercially available from Solvay Advanced Polymers, L.L.C. as PRIMOSPIRE® PR-120 polyphenylene.

The polyarylene (P1) has usually a number average molecular weight greater than 1000, preferably greater than 5000, more preferably greater than about 10000 and still more preferably greater than 15000. On the other hand, the number average molecular weight of the polyarylene (P1) is usually below 100000, and preferably below 70000. In a certain embodiment, the number average molecular weight of the polyarylene (P1) is above 35000. In another embodiment, it is of at most 35000; in this embodiment, it is often of at most 25000 and sometimes of at most 20000. The number average molecular weight of a polyarylene, in particular that of the polyarylene (P1), is advantageously determined by: (1) measuring a "relative" number average molecular weight of the polyarylene by Gel Permeation Chromatography (GPC) using polystyrene calibration standards, then (2) dividing the so-measured "relative" number average molecular weight by a factor 2. It is proceeded accordingly because the skilled in the art who is a specialist of polyarylenes knows that their "relative" number average molecular weight, as measured by GPC, are generally off by a factor of about 2 times; it has already been accounted for this correction factor in all the above cited lower and upper limits of molecular weight.

The polyarylene (P1) can be amorphous (i.e. it has no melting point) or semi-crystalline (i.e. it has a melting point). It is preferably amorphous.

The polyarylene (P1) has a glass transition temperature of advantageously above 50° C., preferably above 120° C. and more preferably above 150° C.

The polyarylene (P1) can be prepared by any method. Methods well known in the art to prepare the polyarylene (P1) are described notably in U.S. Pat. Nos. 5,227,457; 5,539,048; 5,565,543; 5,646,231; 5,654,392; 5,659,005; 5,668,245; 5,670,564; 5,721,335; 5,756,581; 5,760,131; 5,824,744; 5,827,927; 5,869,592; 5,886,130; and 6,087,467, the whole content of which is incorporated herein by reference. A suitable method for preparing the polyarylene (P1) comprises polymerizing, preferably by reductive coupling, at least one dihaloarylene molecular compound consisting of one optionally substituted arylene group, which is linked on each of its two ends to one halogen atom, such as chlorine, bromine and iodine. The elimination of both halogen atoms from a dihaloarylene molecular compound results in the formation of an optionally substituted arylene group, suitable as a recurring unit (R1) of the polyarylene (P1).

Thus, for example:

the elimination of both chlorine atoms from one molecule of p-dichlorobenzene, p-dichlorobiphenyl and their homologous of general formula Cl-($\phi$)$_N$-Cl, N being an integer from 3 to 10, results in the formation of respectively 1, 2 or N adjacent p-phenylene units; thus, p-dichlorobenzene, p-dichlorobiphenyl and their homologous of general formula Cl-($\phi$)$_N$-Cl, N as above defined, can be polymerized, so as to form p-phenylene units;

2,5-dichlorobenzophenone (p-dichlorobenzophenone) can be polymerized, so as to form 1,4-(benzoylphenylene) units;

2,5-dichloro-4'-phenoxybenzophenone can be polymerized, so as to form 1,4-(4'-phenoxybenzoylphenylene) units;

m-dichlorobenzene can be polymerized, so as to form m-phenylene units.

The polymer composition of the present invention can comprise one and only one polyarylene (P1). Alternatively, it can comprise two, three, or even more than three polyarylenes (P1).

The poly(aryl ether ketone) (P2)

For the purpose of the present invention, the term "poly(aryl ether ketone)" is intended to denote any polymer of which more than 50 wt. % of the recurring units are recurring units (R2) comprising at least one carbonyl group in-between two arylene groups, said recurring units (R2) being of one ore more of the following formulae:

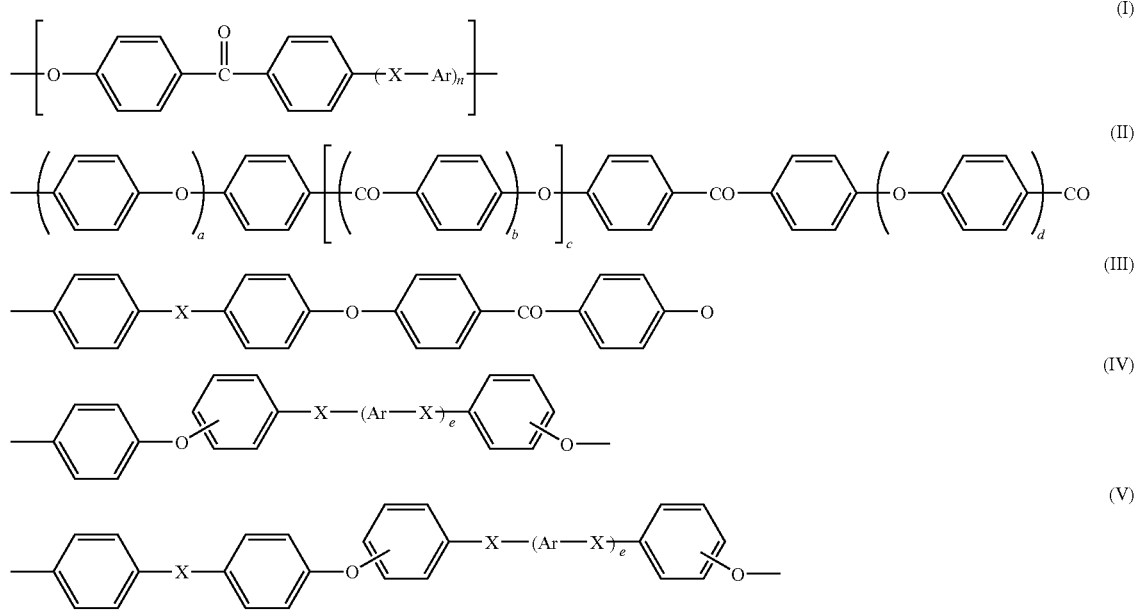
wherein:
Ar is independently a divalent aromatic radical selected from phenylene, biphenylene or naphthylene,
X is independently O, C(=O) or a direct bond,
n is an integer of from 0 to 3,
b, c, d and e are 0 or 1,
a is an integer of 1 to 4, and
preferably, d is 0 when b is 1.
Recurring units (R2) may notably be chosen from:
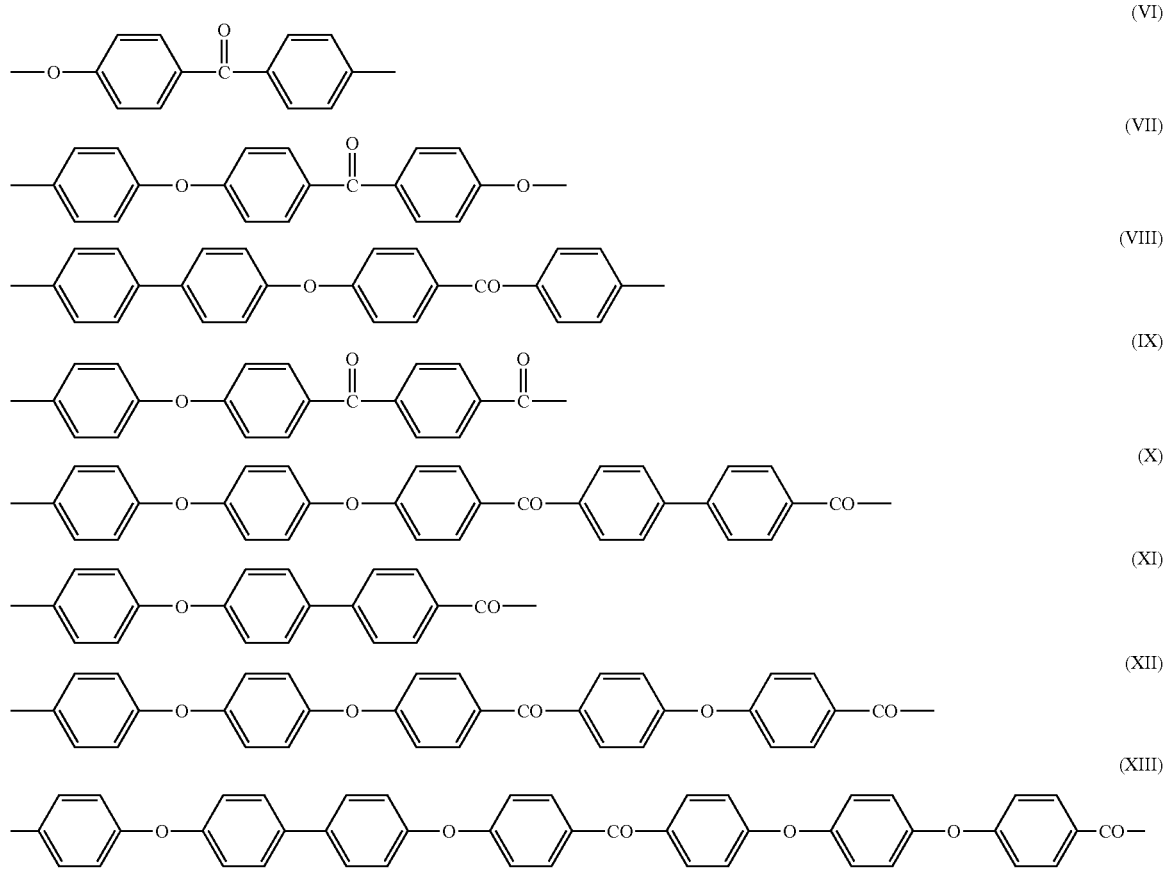

-continued

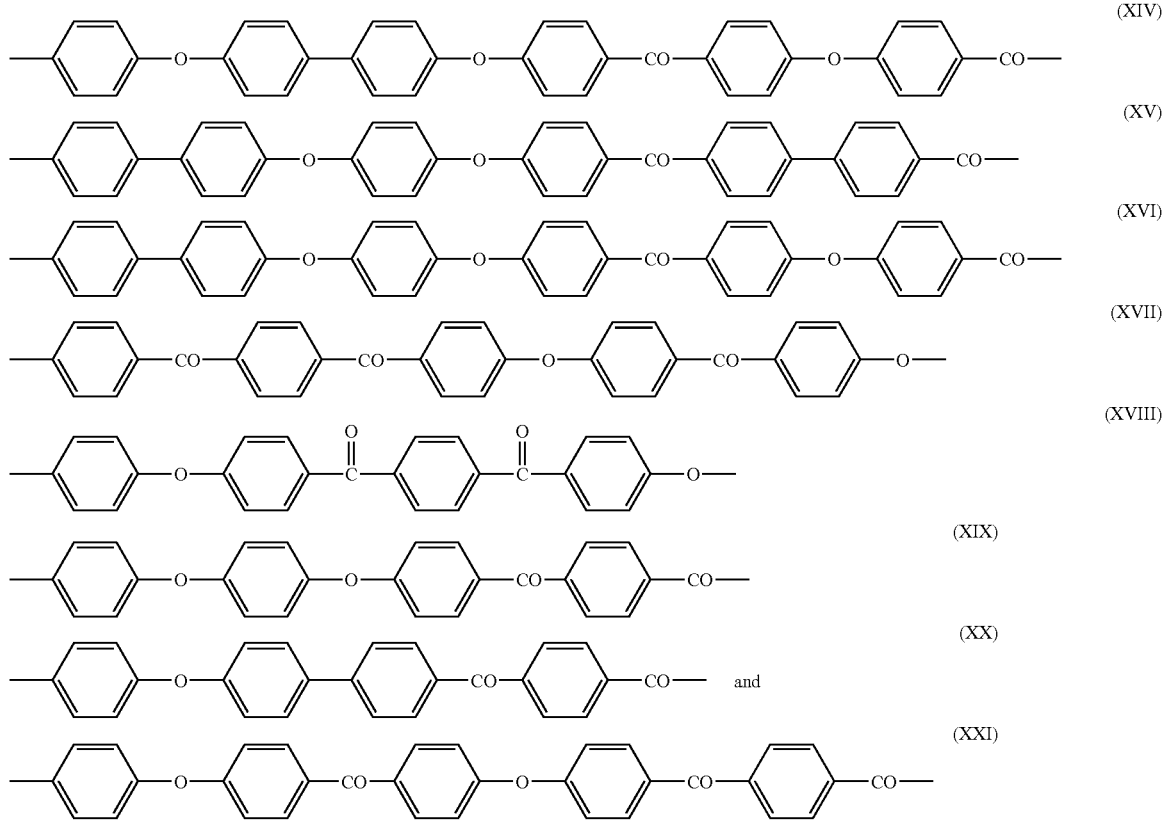

Preferably, recurring (R2) are chosen from:

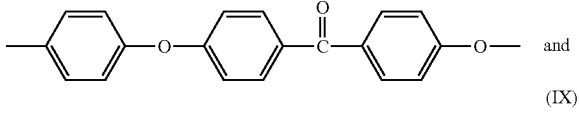
(VII)
and
(IX)

More preferably, recurring units (R2) are:

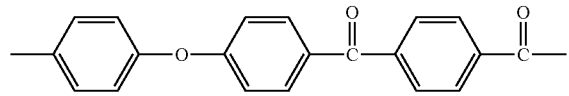
(VII)

For the purpose of the present invention, a poly(ether ether ketone) is intended to denote any polymer of which more than 50 wt. % of the recurring units are recurring units (R2) of formula (VII).

Preferably more than 70 wt. %, and more preferably more than 85 wt. % of the recurring units of the poly(aryl ether ketone) (P2) are recurring units (R2). Still more preferably, essentially all the recurring units of the poly(aryl ether ketone) (P2) are recurring units (R2). Most preferably, all the recurring units of the poly(aryl ether ketone) (P2) are recurring units (R2).

Excellent results are obtained when the poly(aryl ether ketone) (P2) is a poly(ether ether ketone) homopolymer, i.e. a polymer of which essentially all, if not all, the recurring units are of formula (VII). VICTREX® 150 P and VICTREX® 450 P PEEKs from Victrex Manufacturing Ltd., and KETASPIRE® and GATONE® PEEKs from Solvay Advanced Polymers, L.L.C. are examples of poly(ether ether ketone) homopolymers. ZENIVA™ poly(ether ether ketone) is an another example of a PEEK homopolymer commercially available from Solvay Advanced Polymers, L.L.C.; like PRONIVA™ polyphenylene, ZENIVA™ poly(ether ether ketone) forms part of the family of SOLVIVA™ Biomaterials, which are offered for use in particular in implantable medical devices. It goes without saying that ZENIVA™ poly(ether ether ketone), like any other SOLVIVA™ Biomaterial, is manufactured by carefully validated processes, is subject to enhanced controls to provide product traceability, and is tested in an accredited lab.

The poly(aryl ether ketone) (P2) has advantageously a reduced viscosity (RV) of at least 0.60 dl/g, as measured in 95-98% sulfuric acid (d=1.84 g/ml) at a poly(aryl ether ketone) concentration of 1 g/100 ml. The measurement is performed using a No 50 Cannon-Fleske viscometer. RV is measured at 25° C. in a time less than 4 hours after dissolution, to limit sulfonation. The RV of the poly(aryl ether ketone) (P2) is preferably of at least 0.65 dl/g, more preferably of 0.70 dl/g. Besides, the RV of the poly(aryl ether ketone) (P2) is advantageously of at most 1.20 dl/g, preferably at most 1.10 and still more preferably at most 1.00 dl/g.

The poly(aryl ether ketone) (P2) can be amorphous (i.e. it has no melting point) or semi-crystalline (i.e. it has a melting point). It is usually semi-crystalline; the case being, the melting point of the poly(aryl ether ketone) (P2) is advantageously greater than 150° C., preferably greater than 250° C., more preferably greater than 300° C. and still more preferably greater than 325° C.

The poly(aryl ether ketone) (P2) can be prepared by any method.

One well known in the art method contains reacting a substantially equimolar mixture of at least one bisphenol and at least one dihalobenzoid compound or at least one halophenol compound as described in Canadian Pat. No. 847,963. Non limitative example of bisphenols useful in such a process are hydroquinone, 4,4'-dihydroxybiphenyl and 4,4'-dihydroxybenzophenone; non limitative examples of dihalobenzoid compounds useful in such a process are 4,4'-difluorobenzophenone, 4,4'-dichlorobenzophenone and 4-chloro-4'-fluorobenzophenone; non limitative examples of halophenols compounds useful in such a process are 4-(4-chlorobenzoyl)phenol and (4-fluorobenzoyl)phenol. Accordingly, PEEK homopolymers may notably be produced by the nucleophilic process as described in, for example, U.S. Pat. No. 4,176,222, the whole content of which is herein incorporated by reference.

Another well known in the art method to produce PEEK homopolymers comprises electrophilically polymerizing phenoxyphenoxybenzoic acid, using an alkane sulfonic acid as solvent and in the presence of a condensing agent, as the process described in U.S. Pat. No. 6,566,484, the whole content of which is herein incorporated by reference. Other poly(aryl ether ketone)s may be produced by the same method, starting from other monomers than phenoxyphenoxybenzoic acid, such as those described in U.S. Pat. Appl. 2003/0130476, the whole content of which is also herein incorporated by reference.

The polymer composition of the present invention may comprise one and only one poly(aryl ether ketone) (P2). Alternatively, it can comprise two, three, or even more than three poly(aryl ether ketone)s (P2). Certain preferred mixes of poly(aryl ether ketone)s (P2) are:

mixes consisting of (i) at least one poly(aryl ether ketone) (P2a) of which more than 50 wt. % of the recurring units, preferably essentially all the recurring units, and still more preferably all the recurring units are of formula

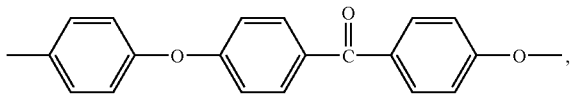

(VII)

with (ii) at least one poly(aryl ether ketone) (P2b) of which more than 50 wt. % of the recurring units, preferably essentially all the recurring units, and still more preferably all the recurring units are of formula

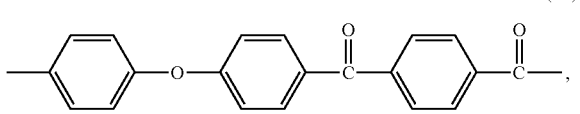

(IX)

and, optionally in addition, with (iii) at least one other poly(aryl ether ketone) (P2c) different from poly(aryl ether ketone)s (P2a) and (P2b);

in particular, mixes consisting of (i) at least one poly(aryl ether ketone) (P2a) of which essentially all, if not all, the recurring units are of formula (VII) with (ii) at least one poly(aryl ether ketone) (P2b) of which essentially all, if not all, the recurring units are of formula (IX);

still more particularly, binary mixes consisting of (i) one poly(aryl ether ketone) (P2a) of which all the recurring units are of formula (VII) with (ii) one poly(aryl ether ketone) (P2b) of which all the recurring units are of formula (IX).

The poly(aryl ether sulfone) (P3)

For the purpose of the invention, a poly(aryl ether sulfone) is intended to denote any polymer, generally a polycondensate, of which more than 50 wt. % of the recurring units are recurring units (R3) of one or more formulae containing at least one arylene group, at least one and at least one ether group (—O—) and at least one sulfone group [—S(=O)$_2$—].

Non limitative examples of poly(aryl ether sulfone)s are polymers of which more than 50 wt. %, up to 100 wt. %, of the recurring units are recurring units (R3) of formula (A) and/or (B):

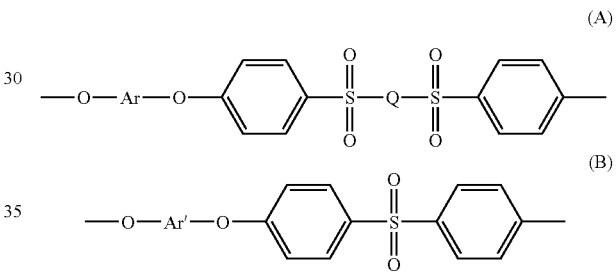

wherein:
Q is a group chosen among the following structures:

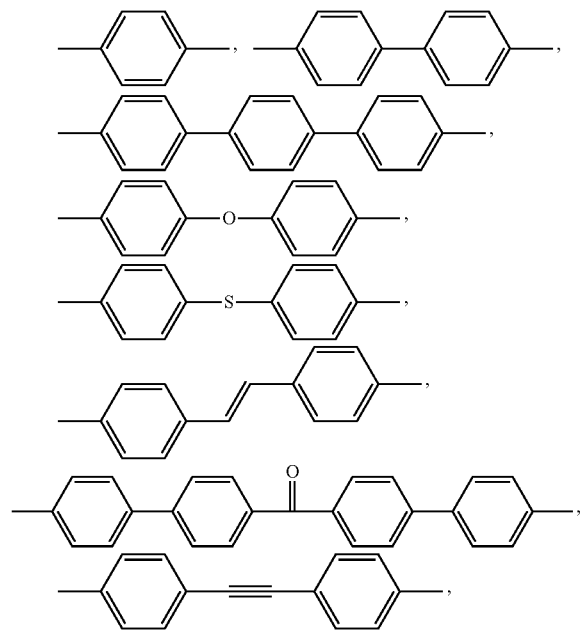

-continued

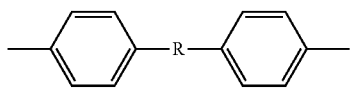

with R being:

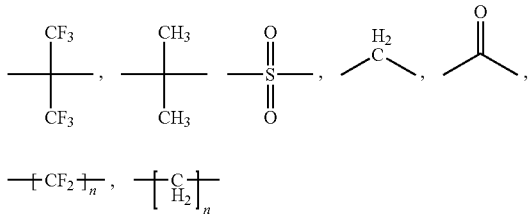

with n=integer from 1 to 6, or an aliphatic divalent group, linear or branched, of up to 6 carbon atoms;
and mixtures thereof;
Ar is a group chosen among the following structures:

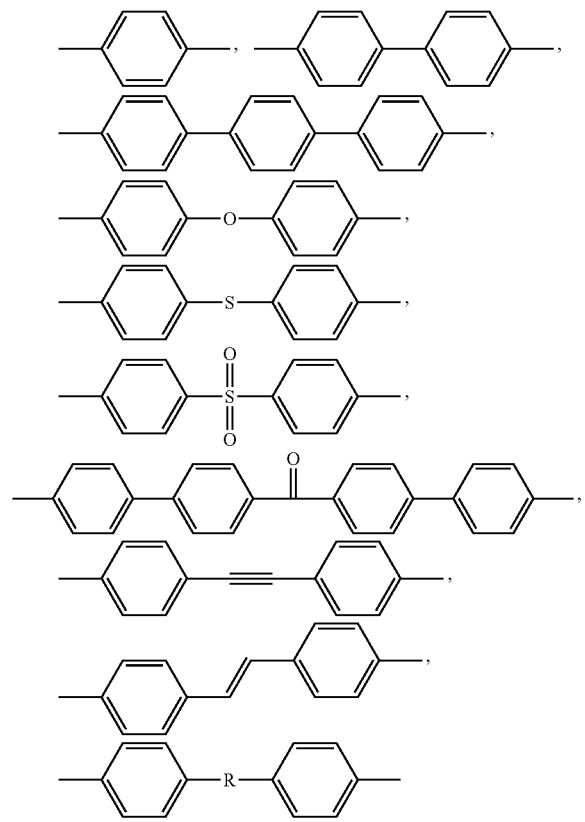

with R being:

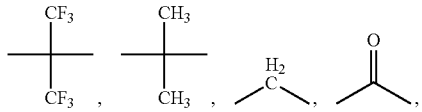

-continued

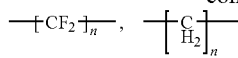

with n=integer from 1 to 6, or an aliphatic divalent group, linear or branched, of up to 6 carbon atoms;
and mixtures thereof;
Ar' is a group chosen among the following structures:

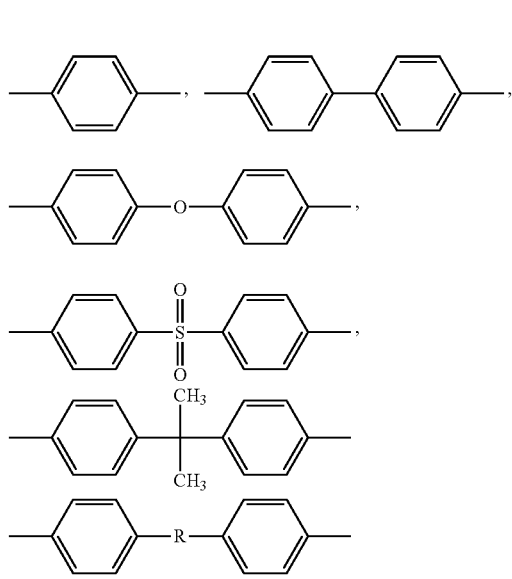

with R being:

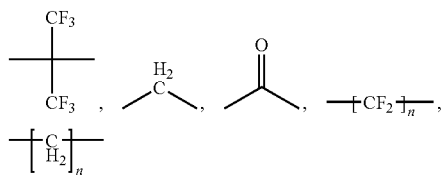

with n=integer from 1 to 6, or an aliphatic divalent group, linear or branched, of up to 6 carbon atoms;
and mixtures thereof.

Among such polymers, it can be particularly cited polymers of which more than 50 wt. %, up to 100 wt. %, of the recurring units are recurring units of one or more of formulae (C), (D), (E) and (F):

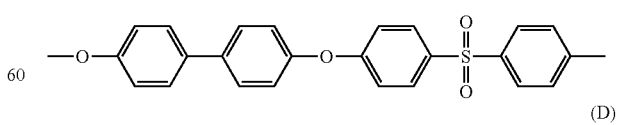
(C)

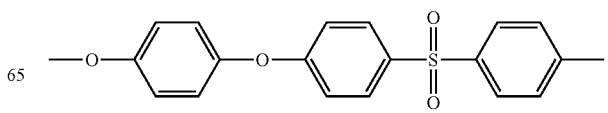
(D)

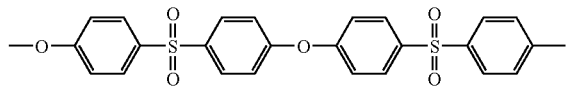
(E)

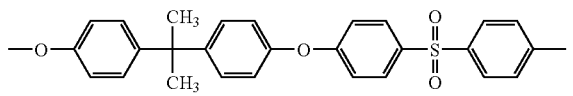
(F)

Polymers comprising more than 50 wt. % of recurring units of formula (C) are commonly known as "polyphenylsulfones" and are commercially available notably from Solvay Advanced Polymers, L.L.C. as RADEL® R poly(aryl ether sulfone)s.

Polymers comprising more than 50 wt. % of recurring units of formula (D) are commonly known as "polyethethersulfones".

Polymers comprising more than 50 wt. % of recurring units of formula (E) are commonly known as polyethersulfones and are commercially available notably from Solvay Advanced Polymers, L.L.C. as RADEL® A poly(aryl ether sulfone)s.

Polymers comprising more than 50 wt. % of recurring units of formula (F) are commonly known as "bisphenol A polysulfones" (or just "polysulfones") and are commercially available notably from Solvay Advanced Polymers, L.L.C. as UDEL®.

The polymer composition may contain one and only one poly(aryl ether sulfone) (P3). Alternatively, the polymer composition may contain two or more one poly(aryl ether sulfone)s (P3); for example, it may contain at least one polyphenylsulfone and at least one polysulfone, or at least one polyphenylsulfone and at least one polyethersulfone.

The poly(aryl ether sulfone) (P3) can be prepared by any method. Methods well known in the art are those described in U.S. Pat. Nos. 3,634,355; 4,008,203; 4,108,837 and 4,175,175, the whole content of which is herein incorporated by reference.

Embodiment (E1)

In a certain embodiment (E1) of the present invention, the poly(aryl ether sulfone) (P3) is a poly(biphenyl ether sulfone).

For the purpose of the present invention, a poly(biphenyl ether sulfone) is intended to denote a polymer of which more than 50 wt. % of the recurring units are recurring units (R3) of one ore more formulae containing at least one p-phenylene group:

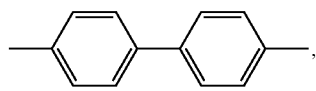

at least one ether group (—O—) and at least one sulfone group [—S(=O)$_2$—].

Recurring units (R3) are preferably of one ore more formulae of the general type:

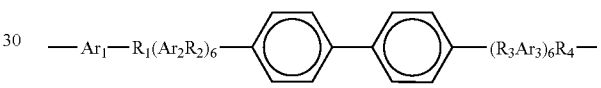
(G)

wherein $R_1$ through $R_4$ are —O—, —SO$_2$—, —S—, —CO—, with the proviso that at least one of $R_1$ through $R_4$ is —SO$_2$— and at least one of $R_1$ through $R_4$ is —O—; $Ar_1$, $Ar_2$ and $Ar_3$ are arylene groups containing 6 to 24 carbon atoms, and are preferably phenylene or p-biphenylene; and a and b are either 0 or 1.

More preferably, recurring units (R3) are chosen from

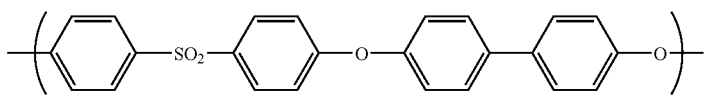
(H)

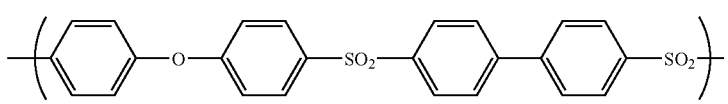
(I)

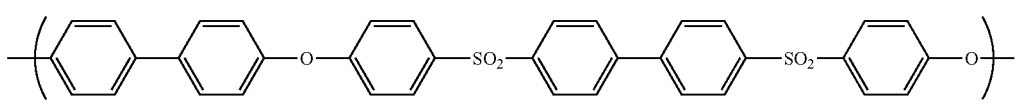
(J)

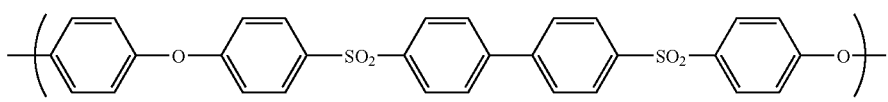
(K)

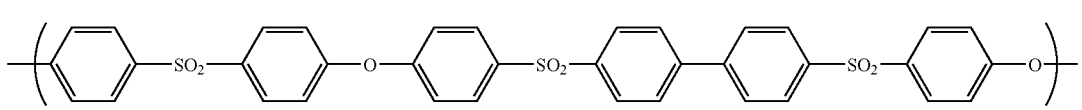
(L)

and mixtures thereof.

Still more preferably, recurring units (R3) are chosen from

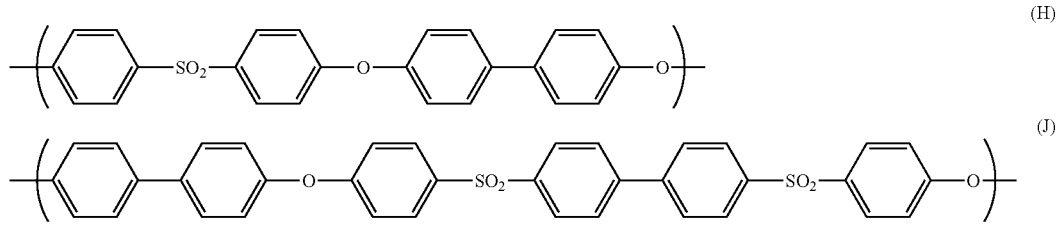

and mixtures thereof.

For the purpose of the present invention, a PPSU polymer is intended to denote any polymer of which more than 50 wt. % of the recurring units are recurring units (R3) of formula (H).

The poly(biphenyl ether sulfone) may be notably a homopolymer or a copolymer such as a random or block copolymer. When the poly(biphenyl ether sulfone) is a copolymer, its recurring units may notably be composed of (i) recurring units (R3) of at least two different formulae chosen from formulae (H) to (L), or (ii) recurring units (R3) of one or more formulae (H) to (L) and recurring units (R3*), different from recurring units (R3), such as:

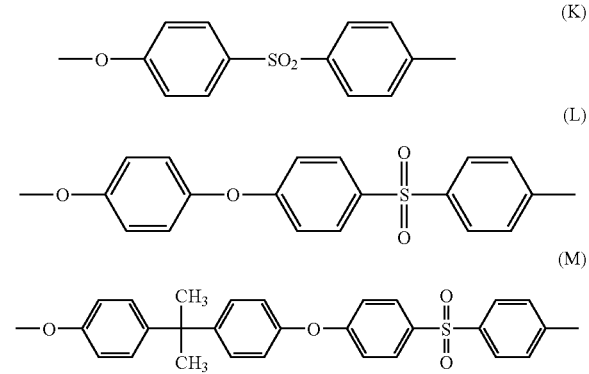

and mixtures thereof.

Preferably more than 90 wt. %, and more preferably more than 95 wt. % of the recurring units of the poly(biphenyl ether sulfone) are recurring units (R3). Still more preferably, all the recurring units of the poly(biphenyl ether sulfone) are recurring units (R3).

Excellent results are obtained when the poly(biphenyl ether sulfone) is a PPSU homopolymer, i.e. a polymer of which all the recurring units are of formula (H). RADEL® R polyphenylsulfone from Solvay Advanced Polymers, L.L.C. is an example of a PPSU homopolymer. VERIVA™ polyphenylsulfone is an another example of a PPSU homopolymer commercially available from Solvay Advanced Polymers, L.L.C.; like PRONIVA™ and ZENIVA™ polymers, VERIVA™ polyphenylsulfone forms part of the family of SOLVIVA™ Biomaterials, which are offered for use in particular in implantable medical devices. It goes without saying that VERIVA™ polyphenylsulfone, like any other SOLVIVA™ Biomaterial, is manufactured by carefully validated processes, is subject to enhanced controls to provide product traceability, and is tested in an accredited lab.

The poly(biphenyl ether sulfone) can be prepared by any method. Methods well known in the art are those described in U.S. Pat. Nos. 3,634,355; 4,008,203; 4,108,837 and 4,175,175, the whole content of which is herein incorporated by reference.

Embodiment (E2)

In a certain embodiment (E2) of the present invention, the poly(aryl ether sulfone) is a polysulfone.

To the purpose of the present invention, a polysulfone is intended to denote any polymer of which more than 50 wt. % of the recurring units are recurring units (R3) of one or more formulae containing at least one ether group (—O—), at least one sulfone group (—SO$_2$—) et at least one group as shown hereafter:

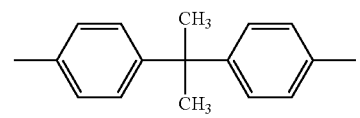

Preferably, recurring units (R3) are chosen from

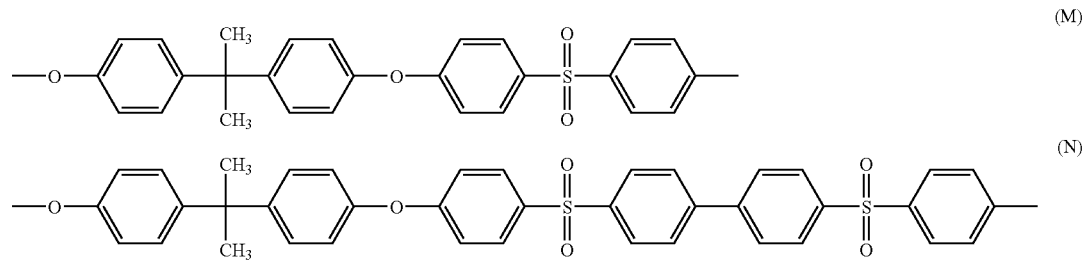

and mixtures thereof.

Very preferably, recurring units (R2) are

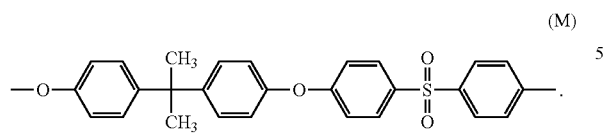
(M)

The polysulfone may notably be a homopolymer, a copolymer such as a random or block copolymer. When the polysulfone is a copolymer, its recurring units may notably be composed of (i) recurring units (R3) of formulas (M) and (N), or
(ii) on one hand, recurring units (R3) of at least one of formulas (M) and (N), and, on the other hand, recurring units (R3*), different from recurring units (R3), such as

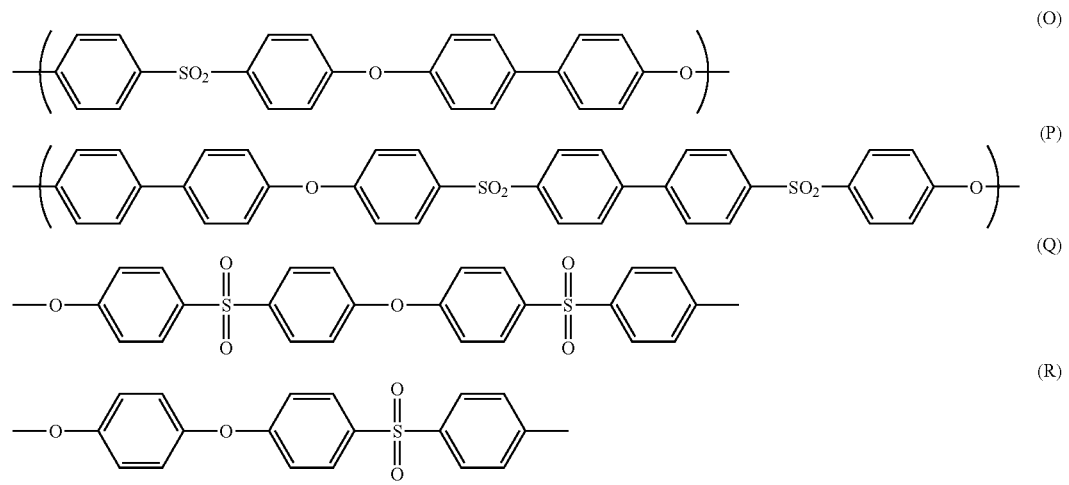
(O)
(P)
(Q)
(R)

and mixtures thereof.

Preferably more than 90 wt. %, and more preferably more than 95 wt. % of the recurring units of the polysulfone are recurring units (R3). Still more preferably, all the recurring units of the polysulfone are recurring units (R3).

The most preferred polysulfone is a homopolymer of which the recurring units are recurring units (R3) of formula

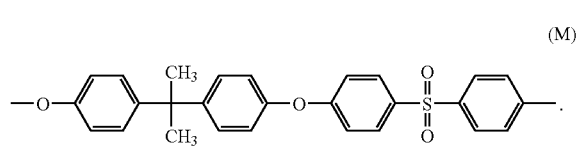
(M)

Such a polysulfone homopolymer is notably commercialized by Solvay Advanced Polymers, L.L.C. under the trademark UDEL®.

Embodiment (E3)

In a certain embodiment (E3) of the present invention, the poly(aryl ether sulfone) is a polyethersulfone.

To the purpose of the present invention, a polyethersulfone is intended to denote any polymer of which more than 50 wt. % of the recurring units are recurring units (R3) of formula

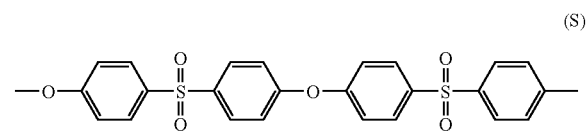
(S)

The polyethersulfone may be notably a homopolymer, or a copolymer such as a random or a block copolymer. When the polyethersulfone is a copolymer, its recurring units are advantageously a mix of recurring units (R3) of formula (S) and of recurring units (R3*), different from recurring units (R3), such as:

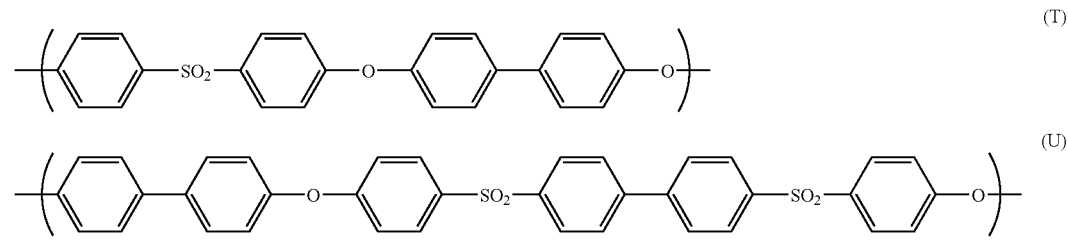
(T)
(U)

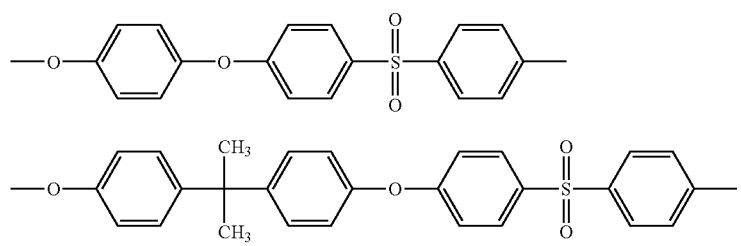

(V)

(W)

and mixtures thereof.

Preferably, the polyethersulfone is a homopolymer, or it is a copolymer the recurring units of which are a mix composed of recurring units (R3) of formula (S) and of recurring units (R3*) of formula (T), or it can also be a mix of the previously cited homopolymer and copolymer.

Solvay Advanced Polymers, L.L.C. commercializes various polyethersulfones under the trademark RADEL® A.

Embodiment (E4)

In a certain embodiment (E4) of the present invention, the poly(aryl ether sulfone) is a polyimidoethersulfone.

For the purpose of the present invention, a polyimidoethersulfone is intended to denote a polymer of which at least 5 wt. % of the recurring units are recurring units (R3) of formula (X), (Y) and/or (Z), as represented below:

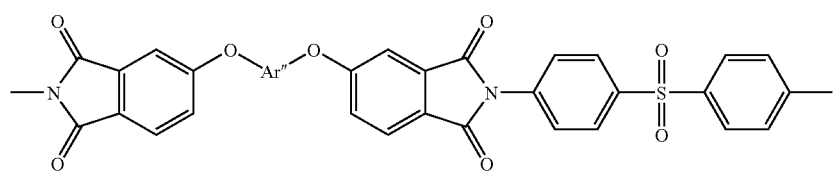

(X)

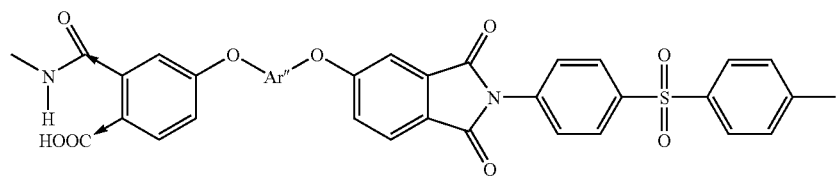

(Y)

(Z)

wherein:

(Y) and (Z) are the auric acid forms corresponding to the imide form (X);

the → denotes isomerism so that in any recurring unit the groups to which the arrows point may exist as shown or in an interchanged position;

Ar″ is chosen among the following structures:

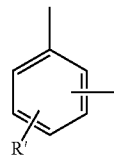

with the linking groups being in ortho, meta or para position and R′ being a hydrogen atom or an alkyl radical comprising from 1 to 6 carbon atoms,

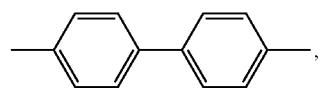

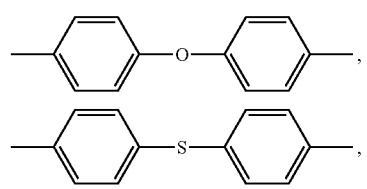

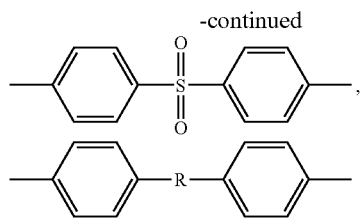

with R being an aliphatic divalent group of up to 6 carbon atoms, such as methylene, ethylene, isopropylene and the like, and mixtures thereof.

Preferably more than 50 wt. %, and more preferably more than 90 wt. % of the recurring units of the polyimidoethersulfone are recurring units (R3). Still more preferably, all the recurring units of the polyimidoethersulfone are recurring units (R3).

For certain particular applications, embodiment (E1) is preferred. This closes the discussion on embodiments (E1) to (E4).

The weight of the polyarylene (P1), based on the total weight of the polyarylene (P1), the poly(aryl ether ketone) (P2) and the poly(aryl ether sulfone) (P3) in the polymer composition, is advantageously of at least 10%, preferably at least 15%, more preferably at least 20%, still more preferably at least 30% and most preferably at least 40%. On the other hand, the weight of the polyarylene (P1), based on the total weight of the polyarylene (P1), the poly(aryl ether ketone) (P2) and the poly(aryl ether sulfone) (P3) in the polymer composition, is advantageously of at most 90%, preferably at most 80%, and more preferably at most 70%.

The weight of the poly(aryl ether ketone) (P2), based on the total weight of the polyarylene (P1), the poly(aryl ether ketone) (P2) and the poly(aryl ether sulfone) (P3) in the polymer composition, is advantageously of at least 10%, preferably at least 20% and more preferably at least 30%. On the other hand, the weight of the poly(aryl ether ketone) (P2), based on the total weight of the polyarylene (P1), the poly(aryl ether ketone) (P2) and the poly(aryl ether sulfone) (P3) in the polymer composition, is advantageously of at most 85%, preferably at most 70%, more preferably at most 60%, still more preferably at most 50% and most preferably at most 40%.

The weight of the poly(aryl ether sulfone) (P3), based on the total weight of the polyarylene (P1), the poly(aryl ether ketone) (P2) and the poly(aryl ether sulfone) (P3) in the polymer composition, is advantageously of at least 10%, preferably at least 20% and more preferably at least 30%. On the other hand, the weight of the poly(aryl ether sulfone) (P3), based on the total weight of the polyarylene (P1), the poly(aryl ether ketone) (P2) and the poly(aryl ether sulfone) (P3) in the polymer composition, is advantageously of at most 85%, preferably at most 70%, more preferably at most 60%, still more preferably at most 50% and most preferably at most 40%.

The polymer composition may further contain a variety of other polymers, additives, fillers, and the like, collectively called ingredients. Conventional ingredients of polyarylene, poly(aryl ether ketone) and poly(aryl ether sulfone) compositions, include fibrous reinforcing agents, particulate fillers and nucleating agents such as talc and silica, adhesion promoters, compatibilizers, curing agents, lubricants, metal particles, mold release agents, organic and/or inorganic pigments like $TiO_2$ and carbon black, dyes, flame retardants, smoke-suppressing agents, heat stabilizers, antioxidants, UV absorbers, tougheners such as rubbers, plasticizers, anti-static agents, melt viscosity depressants such as liquid crystalline polymers and the like.

The weight of said optional ingredients, based on the total weight of the polymer composition, is advantageously below 75%, preferably below 50%, more preferably below 25% and still more preferably below 10%. Excellent results are obtained when the polymer composition is essentially free, or even is completely free, of said optional ingredients.

In particular, the polymer composition may further contain a fibrous reinforcing agent, in particular an inorganic fibrous reinforcing agent such as glass fiber and carbon fiber. Thus, in a certain particular non preferred embodiment, the polymer composition comprises from 10 to 50 wt. %, in particular from 20 to 30 wt. %, of a reinforcing agent (all percentages based on the total weight of the blend); an example of such a polymer composition is one composed of 35 wt. % of a kinked rigid-rod polyphenylene homopolymer, 35 wt. % of a poly(ether ether ketone) homopolymer and 30 wt. % of glass fiber. On the other hand, preference is given to a polymer composition wherein the weight of fibrous reinforcing agent, based on the total weight of the polymer composition, is below 10% and preferably below 5%, and excellent results are obtained when the polymer composition is essentially free, or even is completely free, of any fibrous reinforcing agent.

It was surprisingly found that, in spite of substantial discrepancies in their molecular structure, the polyarylene (P1) and the polyarylethers (P2) or (P3) contained in polymer composition were in general at least partially miscible with each other, the miscible portion of these polymers forming then a single phase [(P1) being solubilized in (P2) or ((P3) or the contrary, depending on the relative amounts of polymers].

Also surprisingly, the prosthetic device of the present invention exhibits an excellent balance of properties, including:
very high strength,
very high stiffness,
good elongation properties,
good melt processability (in particular, they are well suited for injection molding applications), and
high chemical resistance.
good biocompatibility;
outstanding impact resistance, as possibly characterized by a standard no-notch IZOD test (ASTM D-4812).

In fact, the Applicant has found out an unexpected synergistic behavior related to the impact resistance of the invented prosthetic devices. They exhibit an outstanding impact resistance generally higher than that of the same prosthetic device made of neat polyarylene, neat poly(aryl ether ketone) or neat poly(aryl ether sulfone) taken individually.

In a preferred embodiment, the prosthetic devices of the present invention are made of a material comprising high purity polyarylene (P1).

Typical polyarylene contaminants are Ni, Zn and P.

High purity polyarylene (P1) contains advantageously less than 10 ppm of Ni, preferably less than 9 ppm, more preferably less than 8 ppm, still more preferably less than 6 ppm and most preferably less than 2 ppm Ni.

High purity polyarylene (P1) contains advantageously less than 200 ppm of Zn, preferably less than 150 ppm, more preferably less than 100 ppm, still more preferably less than 80 ppm and most preferably less than 50 ppm Zn.

High purity polyarylene (P1) contains advantageously less than 1000 ppm of P, preferably less than 800 ppm, more preferably less than 700 ppm, still more preferably less than 600 ppm and most preferably less than 500 ppm P.

High purity polyarylene (P1) contains preferably at the same time less than 5 ppm Ni, less than 50 ppm Zn and less than 800 ppm P.

High purity polyarylenes may be obtained from prior art processes, such as the one described in WO93/04099, WO93/14055, WO96/39455, WO2005/072374, the content of which are herein incorporated by reference. Additional treatments are preferably further carried out to such processes, and the reaction mixture obtained after polymerization is preferably treated as follows. The reaction mixture is then precipitated in an anti-solvent and then the polymer is isolated. The polymer is then washed multiple times with the anti-solvent to extract the residual dissolved catalysts which are converted to the metal salts which are soluble in the anti-solvents. Examples of anti-solvents are ethanol, propanol, 2-butanone, aceton, methanol, isopropanol and mixtures thereof. Mixtures of these anti-solvents with water or acidic aqueous solutions gave also good results. Excellent results were obtained using aceton, methanol, isopropanol. Such specific washing treatment leads advantageously to the obtention of high purity polyarylenes comprising low quantities of residuals, which make them especially well suited for their use in medical applications and in particular for the manufacture of prosthetic devices. High purity polyarylenes (P1) feature excellent mechanical properties and a good biocompatibility which make them excellent candidates for medical applications.

High purity poly(aryl ether ketone) (P2) and poly(aryl ether sulfone) (P3) are also preferred.

A high purity polymer is intended to denote a polymer featuring a purity of above 95%, preferably 98% and more preferably 99%.

Another object of the present invention is thus related to the use of a polymer composition comprising at least one high purity polyarylene (P1) and at least one high purity polyarylether selected from the group consisting of poly(aryl ether ketone)s (P2) and poly(aryl ether sulfone)s (P3) in medical applications. Such polymer composition is especially well suited for the manufacture of medical application devices such as bone replacement applications, fibers and films for medical applications, fixation devices and medical instruments.

The following examples are included to provide additional guidance to those skilled in the art in practicing the claimed invention. The examples provided are merely representative of the work that contributes to the teaching of the application. Accordingly, these examples are not intended to limit the invention, as defined in the appended claims, in any manner.

Examples

First Set of Examples

The following polymers were used to illustrate some of the surprising behaviors related to the specific compositions used for the manufacture of the invented prosthetic devices:

- a polyphenylene copolymer essentially all, if not all, the recurring units of which consisted of a mix of p-phenylene substituted by a phenylketone group with unsubstituted m-phenylene in a mole ratio p-phenylene:m-phenylene of about 50:50, commercially available from Solvay Advanced Polymers, L.L.C. as PRIMOSPIRE® PR-250 polyphenylene,
- a polyphenylene copolymer essentially all, if not all, the recurring units of which consisted of a mix of p-phenylene substituted by a phenylketone group with unsubstituted m-phenylene in a mole ratio p-phenylene:m-phenylene of about 85:15, commercially available from Solvay Advanced Polymers, L.L.C. as PRIMOSPIRE® PR-120 polyphenylene,
- a poly(ether ether ketone) (PEEK) homopolymer, essentially all, if not all, the recurring units are of formula (VII)

(VII)

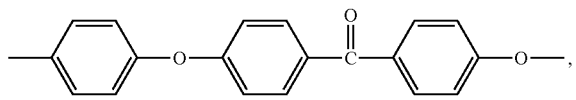

commercially available from Victrex Manufacturing Ltd. as VICTREX® 150 P,

- a polyphenylsulfone (PPSU) homopolymer, essentially all, if not all, the recurring units are of formula (H)

(H)

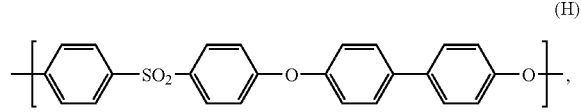

commercially available from SOLVAY ADVANCED POLYMERS, L.L.C as RADEL® R polyphenylsulfone.

CE1 and CE3 and E1 to E3 samples prepared were compounded on a Berstorff 25 mm twin-screw co-rotating intermeshing extruder. CE2 and CE4 as well as E4 and E5 samples were melt-mixed using a 1 inch diameter Killion single screw extruder having a mixing section at a melt temperature of 330° C.

In the case of the neat polymer controls, the compounding step was to convert the resins from powder to pellet form and to impart the same heat history seen by the blends on the corresponding base polymers.

Mechanical property tests were conducted per the ASTM methods indicated using 3.2 mm-thick ASTM specimens: tensile strength, modulus and elongation at yield were tested using ASTM D-638 procedure, flexural strength and modulus were tested using ASTM D-790 procedure, while unnotched Izod impact strength was tested using ASTM D-4812 procedure.

The results are presented in table 1 below.

TABLE 1

|  | CE1 | CE2 | CE3 | CE4 | E1 | E2 | E3 | E4 | E5 |
|---|---|---|---|---|---|---|---|---|---|
| PRIMOSPIRE ® PR-250 polyphenylene (parts by weight) | 100 | 0 | 0 | 0 | 30 | 50 | 70 | 0 | 0 |
| PRIMOSPIRE ® PR-120 polyphenylene (parts by weight) | 0 | 100 | 0 | 0 | 0 | 0 | 0 | 30 | 20 |
| VICTREX ® 150 P poly(ether ether ketone) (parts by weight) | 0 | 0 | 100 | 0 | 70 | 50 | 30 | 0 | 0 |

TABLE 1-continued

|  | CE1 | CE2 | CE3 | CE4 | E1 | E2 | E3 | E4 | E5 |
|---|---|---|---|---|---|---|---|---|---|
| RADEL ® R polyphenylsulfone (parts by weight) | 0 | 0 | 0 | 100 | 0 | 0 | 0 | 70 | 80 |
| Tensile strength (Kpsi) | 23.8 | 30.0 | 14.3 | 8.5 | 14.9 | 17.4 | 19.6 | 14.8 | 13.0 |
| Tensile modulus (Kpsi) | 874 | 1200 | 514 | 330 | 584 | 654 | 723 | 503 | 597 |
| Tensile elongation at yield (%) | No yield | No yield | 5.5 | 15 | 4.4 | 4.6 | 4.8 | 6.0 | 6.3 |
| Flexural strength (Kpsi) | 36.6 | 45.0 | 21.6 | 14.5 | 23.4 | 26.9 | 29.9 | 21.4 | 19.5 |
| Flexural modulus (Kpsi) | 921 | 1200 | 538 | 340 | 594 | 677 | 757 | 500 | 440 |
| Unnotched Izod (ft-lb/in) | 20 | 20 | 16 | No break | 26 | 35 | 32 | 33 | 46 |

Blends (E1) to (E5), especially blends (E2) and (E3), exhibited an excellent balance of properties, including a very high strength and a very high stiffness.

They exhibited also good elongation properties, including when an amount of polyphenylene as high as 70 parts by weight was used, as it is the case for blend (E3).

Finally, the samples (E1) to (E5) exhibited an outstanding impact resistance, as characterized by a standard unnotched IZOD test (ASTM D-4812). In particular, the impact resistance of all the polyarylene-poly(aryl ether ketone) blends (E1) to (E3) was much higher than that of neat polyarylene and neat poly(aryl ether ketone) taken individually (strong synergistic behavior).

Second Set of Examples

Miscibility-related data: $T_g$ measurements and TEM photomicrographs.

On one hand, individual compositions comprising various proportions by weight of PRIMOSPIRE® PR-120 polyphenylene and RADEL® R polyphenylsulfone, which are used for the manufacture of the invented prosthetic devices, were melt-mixed using a 1 inch diameter Killion single screw extruder having a mixing section at a melt temperature of 330° C. The resulting blends were analyzed by DSC, and the results are shown in Table 2.

TABLE 2

| | Example or Comparative Example | | | | | |
|---|---|---|---|---|---|---|
| | CE5 | E6 | E7 | E8 | E9 | CE6 |
| polyphenylsulfone/ polyphenylene | 100/0 | 90/10 | 80/20 | 70/30 | 60/40 | 0/100 |
| $T_{g,1}$ (° C.) | 221 | 219 | 217 | 216 | 216 | — |
| $T_{g,2}$ (° C.) | — | 162 | 164 | 163 | 163 | 158 |

The observed shifts in $T_g$ values suggest that some degree of miscibility between polyphenylene 1 and RADEL® R polyphenylsulfone was surprisingly present.

On the other hand, a transmission electron microscope (TEM) photomicrograph showing the morphology of the blend E2 of the above 1$^{st}$ set of examples is provided in FIG. 7. As a reminder, this blend is composed of 50 parts by weight of PRIMOSPIRE® PR-250 polyphenylene and of 50 parts by weight of VICTREX® 150 P poly(ether ether ketone). The bars shown on the micrograph corresponded to an effective length of 3 μm; the light phase was made of the polyphenylene. As can be seen from the photograph, the PEEK and the polyphenylene form unexpectedly domains having a rather small size and which are dispersed in a substantially homogeneous manner. Without being bound to any theory, this strongly suggests that the PEEK and the polyphenylene are to some extent compatible, when not partially miscible, with each other in spite of substantial discrepancies in the molecular structure of both polymers.

Third Set of Examples

Biocompatibility Test Results

The biocompatibility of a polyarylene copolymer essentially all, if not all, the recurring units of which consisted of a mix of p-phenylene substituted by a phenylketone group with unsubstituted m-phenylene in a mole ratio p-phenylene: m-phenylene of about 50:50, commercially available from Solvay Advanced Polymers, L.L.C. as PRIMOSPIRE® PR-250 polyarylene, was tested using 4 standard tests covering cytotoxicity, sensitization, systemic toxicity and subacute (subchronic toxicity).

ISO Guinea Pig Maximization Sensitization Test Results:

Pellets of the polyarylene were extracted according to ISO 10993-12. The resulting extracts and control blanks were injected to different guinea pigs. On day 6, the dorsal site was reshaved and sodium lauryl sulfate in mineral oil was applied. On day 7, the animals were topically patched with the appropriate test extract and the corresponding blank animals were patched with the corresponding control blank. The patches were removed after 48±2 hours of exposure. Following a 2 week rest period, the animals were topically patched with the appropriate test extract and the corresponding blank animals were patched with the corresponding control blank. The patches were removed after 24±2 hours of exposure. The dermal patch sites were observed for erythema and edema 24±2 and 48±2 hours of exposure. Each animal was assessed for a sensitization response based upon the dermal scores. None of them elicit a sensitization response.

Minimum Essential Medium Elution Using L-929 Mouse Fibroblast Cells (ISO) (Cytotoxicity) Test Results:

Pellets of the polyarylene were extracted at 37±1° C. for 24-25 hours. The extract was inoculated onto the cell line and incubated at 37±1° C. in a humidified atmosphere with 5±1% $CO_2$ in the air. Cultures were evaluated for cytotoxic effects by microscopic observations after 24, 48 and 72 hours incubation periods. The polyarylene was considered non-toxic.

ISO Intracutaneous Reactivity Test:

Pellets of the polyarylene were extracted for 72±2 hours at 37±1° C. Two New Zealand white rabbits (*Oryctolagus* cuniculus) each received 5 sequential 0.2 mL intracutaneous injections along either side of the dorsal mid-line with the test extract on one side and the control extract on the other. The irritations reactions were scored at 24, 48 and 72 hours post-injection on each rabbit for evidence of erythema and edema. The polyarylene was considered as non-irritant.

ISO Acute Systemic Injection Test

Pellets of the polyarylene were extracted for 72±2 hours at 37±2° C. Groups of five albino, Swiss mice (*Mus musculus*) were injected systemically with test or control extracts at a dosing of 50 mL per kg body weight. The animals were observed for signs of toxicity immediately after injection and at 4, 24, 48 and 72 hours post injection. The polyarylene was considered non-toxic.

A panel of biocompatibility tests was also applied to RADEL® R-5000 NT polyphenylsulfone, a poly(aryl ether sulfone) commercially available from SOLVAY ADVANCED POLYMERS, L.L.C., on one hand, and to KetaSpire® KT-820 NT poly(ether ether ketone), a poly (aryl ether ketone) also commercially available from SOLVAY ADVANCED POLYMERS, L.L.C., on the other hand. Based thereon, no evidence of cytotoxicity, sensitization, irritation or acute systemic toxicity was demonstrated.

Should the disclosure of any of the patents, patent applications, and publications that are incorporated herein by reference conflict with the present specification to the extent that it might render a term unclear, the present specification shall take precedence.

The invention has been described with reference to preferred and exemplary embodiments but is not limited thereto. Those skilled in the art will appreciate that various modifications can be made without departing from the scope of the invention, which is defined by the following claims.

The invention claimed is:

1. A prosthetic device comprising at least one part consisting of a polymer composition comprising at least one polyarylene (P1) and at least one polyarylether selected from the group consisting of poly(aryl ether ketone)s (P2) and poly(aryl ether sulfone)s (P3).

2. The prosthetic device according to claim 1, wherein the polyarylene (P1) is a kinked rigid-rod polymer.

3. The prosthetic device according to claim 1, wherein more than 90 wt. % of the recurring units of the polyarylene (P1) are recurring units (R1) of one or more formulae consisting of an optionally substituted phenylene group which is linked by each of its two ends to two other optionally substituted phenylene groups via a direct C—C linkage.

4. The prosthetic device according to claim 3, wherein said recurring units (R1) are a mix of recurring units (R1-a) with recurring units (R1-b), said recurring units (R1-a) being optionally substituted p-phenylenes and said recurring units (R1-b) being optionally substituted m-phenylenes.

5. The prosthetic device according to claim 4, wherein the mole ratio of the recurring units (R1-b), based on the total number of moles of the recurring units (R1-a) and (R1-b), ranges from 30% to 70%.

6. The prosthetic device according to claim 1, wherein the recurring units of the polyarylene (P1) consist of a mix of p-phenylene substituted by a phenylketone group with unsubstituted m-phenylene in a mole ratio p-phenylene:m-phenylene of from 70:30 to 30:70.

7. The prosthetic device according to claim 1, wherein the polyarylether is a poly(aryl ether sulfone) (P3).

8. The prosthetic device according to claim 7, wherein the poly(aryl ether sulfone) (P3) is a polyphenylsulfone.

9. The prosthetic device according to claim 1, wherein the polyarylether is a poly(aryl ether ketone) (P2).

10. The prosthetic device according to claim 9, wherein the poly(aryl ether ketone) (P2) is a poly(ether ether ketone).

11. The prosthetic device according to claim 1, which is suitable to act as replacement of a missing or defective animal or human body part.

12. The prosthetic device according to claim 1, which is suitable to supplement, or to act as reinforcement of a defective body part.

13. The prosthetic device according to claim 1, which is an implantable orthopaedic prosthesis.

14. The prosthetic device according to claim 13, which is selected from the group consisting of hip joints, knee prosthesis and spinal disc orthoprosthesis.

15. The prosthetic device according to claim 1, which is an implant.

16. The prosthetic device according to claim 1, which is a denture or a partial denture.

* * * * *